US011376310B2

(12) United States Patent
Park et al.

(10) Patent No.: US 11,376,310 B2
(45) Date of Patent: Jul. 5, 2022

(54) PHARMACEUTICAL COMPOSITION FOR PREVENTING OR TREATING DENTIN-DENTAL PULP DISEASES OR PERIODONTAL DISEASE INCLUDING CPNE4 PROTEIN

(71) Applicants: HYSENSBIO, Gwacheon-si (KR); SEOUL NATIONAL UNIVERSITY R&DB FOUNDATION, Seoul (KR)

(72) Inventors: Joo Hwang Park, Incheon (KR); Ji Hyun Lee, Seoul (KR); Joo Cheol Park, Seoul (KR); Dong Seol Lee, Seoul (KR)

(73) Assignees: HYSENSBIO, Gwacheon-si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/958,512

(22) PCT Filed: Dec. 17, 2018

(86) PCT No.: PCT/KR2018/016012
§ 371 (c)(1),
(2) Date: Jun. 26, 2020

(87) PCT Pub. No.: WO2019/132353
PCT Pub. Date: Jul. 4, 2019

(65) Prior Publication Data
US 2021/0052699 A1    Feb. 25, 2021

(30) Foreign Application Priority Data
Dec. 28, 2017  (KR) .................. 10-2017-0182391

(51) Int. Cl.
| A61K 38/17 | (2006.01) |
| A61K 48/00 | (2006.01) |
| A61P 1/02 | (2006.01) |
| A23L 33/18 | (2016.01) |
| A23L 33/13 | (2016.01) |
| A23K 20/147 | (2016.01) |
| A23K 20/142 | (2016.01) |
| A23K 20/24 | (2016.01) |

(52) U.S. Cl.
CPC .......... *A61K 38/1738* (2013.01); *A23L 33/18* (2016.08); *A61P 1/02* (2018.01)

(58) Field of Classification Search
CPC .......... A23V 2002/00; A23V 2200/312; A61K 38/1709; A61K 38/1738; A61K 48/00; A61P 1/02; A23K 20/142; A23K 20/147; A23K 20/24; A23L 33/13; A23L 33/18; A23L 33/30
See application file for complete search history.

(56) References Cited

FOREIGN PATENT DOCUMENTS

| KR | 10-2011-0019106 A | 2/2011 |
| KR | 10-2012-0089547 A | 8/2012 |
| KR | 10-2013-0113724 A | 10/2013 |
| KR | 10-2015-0145470 A | 12/2015 |
| KR | 10-1856598 B1 | 5/2018 |

OTHER PUBLICATIONS

KR 2015145470, machine English translation, pp. 1-38. Dec. 30, 2015. (Year: 2015).*
NP_001276041 from NCBI, pp. 1-3, first published 1998. (Year: 1998).*
XP_016878627 from NCBI, pp. 1-2, May 16, 2021. (Year: 2021).*
Choung et al., "Tertiary Dentin Formation after Indirect Pulp Capping Using Protein CPNE7," Journal of Dental Research, 2016, 95(8): 906-912. (Year: 2016).*
International search report for PCT/KR2018/016012 dated Mar. 18, 2019.

* cited by examiner

*Primary Examiner* — Julie Ha
(74) *Attorney, Agent, or Firm* — Sughrue Mion, PLLC

(57) ABSTRACT

Provided are compositions including a CPNE4 protein or a polynucleotide encoding thereof, a pharmaceutical composition, a quasi-drug composition, a dietary supplement, and a health functional food composition. A method for preventing or treating dentin-dental disease or periodontal disease and a method and a method for promoting regeneration of hard tissue including dentin, bone and cementum, and/or pulp tissue are disclosed.

30 Claims, 14 Drawing Sheets
Specification includes a Sequence Listing.

Mineralized tissue formation in vivo

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
attccggttc cccagttagt a                                                 21

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctgttgctag tggtgctgtt                                                   20

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
aggtcggtgt gaacggattt g                                                 21

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
tgtagaccat gtagttgagg tca                                               23

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
caaccataga gaaagcaaac gcg                                               23

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
tttctgttgc cactgctggg ac                                                22

<210> SEQ ID NO 7
<211> LENGTH: 22
<212> TYPE: DNA
<213> ORGANISM: Artificial Sequence

```
<220> FEATURE:
<223> OTHER INFORMATION: Primer

<400> SEQUENCE: 7
agccctgacc actccagttt ag                                              22

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ccctctatgg ctgtttcttt ctct                                            24

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
gaatggcctg tgctttctca a                                               21

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tcggatgagt cactactgcc c                                               21

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
acaggcaaat gaagaccc                                                   18

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
ttcactggct tgtatgg                                                    17

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ccatggagaa ggctgggg                                                   18
```

```
<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
caaagttctc atggatgacc                                              20
```

PHARMACEUTICAL COMPOSITION FOR PREVENTING OR TREATING DENTIN-DENTAL PULP DISEASES OR PERIODONTAL DISEASE INCLUDING CPNE4 PROTEIN

CROSS-REFERENCE TO RELATED APPLICATIONS

This application is a National Stage of International Application No. PCT/KR2018/016012 filed on Dec. 17, 2018, which claims priority under U.S.C. § 119(a) to Korean Patent Application No. 10-2017-0182391 filed on Dec. 28, 2017.

BACKGROUND OF THE INVENTION

1. Field of the Invention

The present invention relates to a Pharmaceutical composition including CPNE4 protein, and more particularly, to and a pharmaceutical composition for preventing or treating dentin-dental pulp diseases and/or periodontal diseases comprising a CPNE4 protein for promoting regeneration of hard tissue including dentin, bone and cementum and/or dental pulp tissues, a gene encoding the protein or an expression vector of the gene, a quasi-drug composition for preventing or alleviating dentin-dental pulp diseases and/or periodontal diseases, and a health functional food composition for preventing or alleviating dentin-dental pulp diseases and/or periodontal diseases.

2. Description of the Related Art

Dental pulp is a richly innervated and vascularized soft connective tissue that occupies the pulp chamber inside a tooth and extends to the outer surface of the dentin. Disorders occurring in the dental pulp are called dental pulp diseases.

There are many causes of dental pulp diseases, but in most cases, dental pulp diseases are caused by a bacterial infection due to dental caries, or infections in the dental pulp through the perforation, fracture, cracks, or periodontal pocket. External wounds, abrasion, tooth cracks, or friction or heat from dental equipment may also cause dental pulp diseases. The pulpitis caused by bacterial infection may lead to root apex and periodontal diseases. Dental pulp diseases successively progress to pulp hyperemia, pulpitis, and pulp necrosis. Pulp necrosis may lead to periapical diseases or disorders to the entire tooth because the death of the dental pulp prevents the blood supply to the dental pulp, and thus the entire pulp tissue is lost.

For treatment of the pulp or periapical diseases, pulp capping materials and pulp canal filling materials are used, and calcium hydroxides, MTA (Mineral Trioxide Aggregate), Gutta-percha, etc., has been generally used. MTA shows therapeutic effects because it has a leakage sealing ability and biocompatibility. However, the use of MTA is hampered due to its relatively high cost as a dental repair material and discoloration, leading to an esthetic problem. Gutta-percha is relatively low cost and has excellent flow characteristics. However, it is not a physiologically acceptable method which causes a loss of viability of the pulp. Up to now, conservative treatments for dentin and pulp diseases have problems of the weak or brittle teeth or reinfection.

Periodontal disease is an inflammatory disease that occurs in the gums, periodontal ligaments, or alveolar bone, the tissue around the teeth that maintains the teeth. It is known that gingivitis and periodontitis cause discomfort that significantly deteriorates the quality of life, and it is difficult to maintain the oral cavity properly, causing plaque deposition and thus causing dental caries and periodontal disease. In addition, in the case of hypersensitivity, the plaque cannot be controlled, and as a result, periodontal disease progresses, and gingival regression increases, causing a vicious cycle in which hypersensitivity becomes more severe.

Since the ultimate goal of treating periodontal disease is to restore damaged connective tissue, cementum and alveolar bone, for this purpose, not only regeneration of the periodontal ligament supporting the alveolar bone but also the regeneration of the alveolar bone and the cementum that can be attached by the periodontal ligament is needed.

Therefore, many studies have been actively conducted to develop therapeutic agents capable of effectively treating dentin-dental pulp diseases and/or periodontal diseases. For example, Korean Patent Publication No. 2012-0089547 discloses a composition for forming hard tissue or regenerating dentin or pulp tissues, including ameloblasts, apical bud cells, or cultures thereof as an active ingredient, and Korean Patent Publication No. 2009-0033643 discloses novel tooth stem cells derived from tooth follicles and a method of culturing the same. Furthermore, Korean Patent Publication No. 2016-0105627 discloses a pharmaceutical composition for treating periodontal disease comprising pre-ameloblast conditioned medium.

Furthermore, CPNE4 protein is a member of the Copine family, a calcium-dependent membrane-binding protein, encoded by the CPNE4 gene. The CPNE4 protein is composed of a $C_2$-$C_2$ domain and a vWMA domain. The $C_2$ domain is known to play a role in two or three Ca2+ binding to help proteins to be structurally stable (Nalefski, Eric A., and Joseph J. Falke. Protein Science 5.12 (1996). vWMA domain is a cell known to be involved in cell adhesion in extracellular matrix proteins and integrin receptors, and it is known to regulate signaling and interaction between intracellular proteins and proteins (Springer, Timothy A. Structure 14.11 (2006): 1611-1616) CPNE4 protein is expressed in most organs. However, it is known to be mainly expressed in the brain, prostate, testis, heart, etc. However, the exact function of CPNE4 protein at the stage of development of each organ and tissue is not known up to now.

The present inventors had made many efforts to develop an agent capable of more effectively treating dentin-dental pulp diseases and/or periodontal diseases, causing damage to alveolar bone and cementum. As a result, it has been clarified that the CPNE4 protein or a polynucleotide encoding thereof increases the effect of promoting regeneration of hard tissue, including dentin, bone and cementum, and/or pulp tissue, thereby completed the present invention.

SUMMARY OF THE INVENTION

Embodiments of the present inventive concepts may provide a pharmaceutical composition for preventing or treating dentin-dental pulp diseases and/or periodontal diseases comprising CPNE4 protein or a polynucleotide encoding thereof.

Embodiments of the present inventive concepts may also provide a method of preventing or treating dentin-dental pulp diseases and/or periodontal diseases, the method including administering the composition to a subject, excluding humans.

Embodiments of the present inventive concepts may also provide a composition for promoting regeneration of hard tissue and/or pulp tissue, including dentin, bone, and cementum, comprising CPNE4 protein or a polynucleotide encoding thereof. Embodiments of the present inventive concepts may also provide a method of promoting regeneration of hard tissue, including dentin, bone, and cementum and/or dental pulp tissue, the method including administering the composition to a subject.

Embodiments of the present inventive concepts may also provide a composition for promoting differentiation of odontoblast, osteoblast, and/or cementoblast comprising CPNE4 protein or a polynucleotide encoding thereof.

Embodiments of the present inventive concepts may also provide a method for promoting the differentiation of odontoblast, osteoblast, and/or cementoblast, administering the composition to a subject, excluding humans.

Embodiments of the present inventive concepts may also provide a quasi-drug composition for preventing or alleviating dentin-dental pulp diseases and/or periodontal diseases, comprising CPNE4 protein or a polynucleotide encoding thereof.

Embodiments of the present inventive concepts may also provide a health functional food composition for preventing or alleviating dentin-dental pulp diseases and/or periodontal diseases, comprising CPNE4 protein or a polynucleotide encoding thereof.

Embodiments of the present inventive concepts may also provide the use of comprising CPNE4 protein or a polynucleotide encoding thereof in preventing or treating dentin-dental pulp diseases and/or periodontal diseases.

Embodiments of the present inventive concepts may also provide the use of comprising CPNE4 protein or a polynucleotide encoding thereof for promoting regeneration of hard tissue and/or pulp tissue.

Embodiments of the present inventive concepts may also provide a pharmaceutical composition for preventing or treating dentin-dental pulp diseases and/or periodontal diseases comprising a CPNE4 protein for promoting regeneration of hard tissue including dentin, bone and cementum and/or dental pulp tissues, a gene encoding CPNE4 protein and an expression vector of the gene.

Embodiments of the present inventive concepts, the dentin-dental pulp disease, may be dentin hypersensitivity, pulp hyperemia, pulpitis, pulp degeneration, and pulp necrosis.

Embodiments of the present inventive concepts, the periodontal disease may be gingivitis, periodontitis, periodontal pocket or periodontal abscess.

Embodiments of the present inventive concepts may also provide a pharmaceutical composition for preventing or treating dental diseases comprising a gene encoding CPNE4 protein and an expression vector of the gene.

Embodiments of the present inventive concepts, the dental disease includes one or more selected from dentin hypersensitivity, pulp hyperemia, pulpitis, pulp degeneration, pulp necrosis, gingivitis, periodontitis, periodontal pocket and periodontal abscess.

Other embodiments, aspects, advantages, and salient features of the disclosure will become apparent to those skilled in the art from the following detailed description, which, taken in conjunction with the annexed drawings, discloses exemplary embodiments of the disclosure.

Effect of the Invention

A pharmaceutical composition of the present invention comprising CPNE4 protein or a polynucleotide encoding thereof exhibits excellent effects of promoting regeneration of hard tissue including dentin, bone and cementum, and/or pulp tissues. Therefore, it may be widely applied to the development of a variety of agents for preventing or treating dentin-dental pulp diseases or for preventing or treating periodontal diseases causing damage to bone and cementum.

DETAILED DESCRIPTION OF THE PREFERRED EMBODIMENTS

Figure 1:
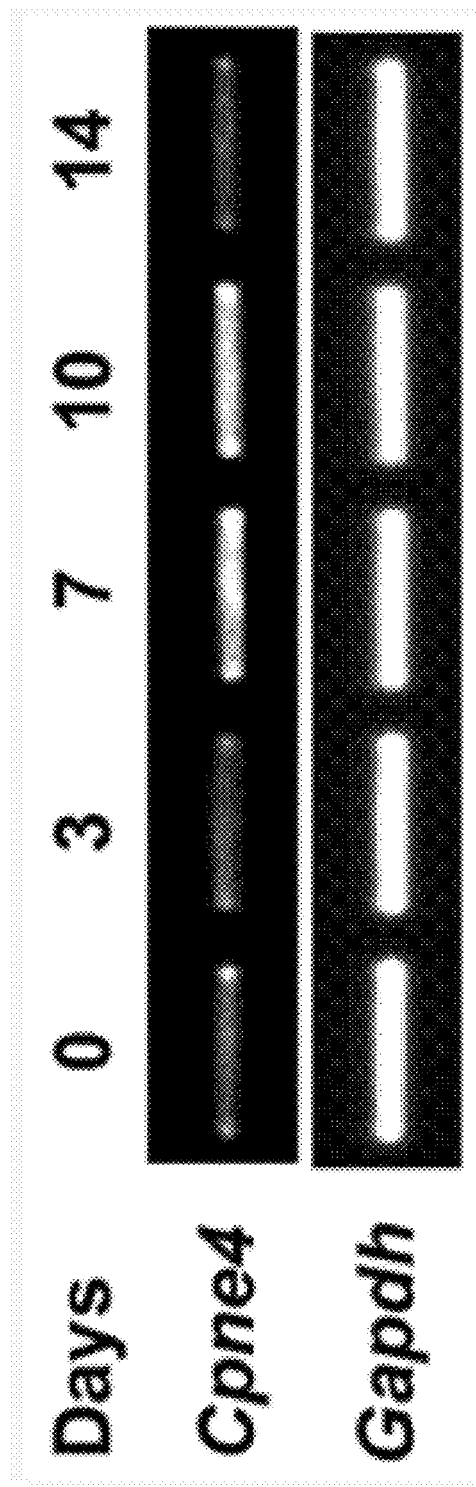
FIG. 1 is a result of confirming the CPNE4 gene expression changes during the odontoblast differentiation process through reverse transcription-polymerase chain reaction (RT-PCR).

The present invention is based on the discovery that CPNE4 increases the effect of promoting regeneration of hard tissue and/or pulp tissue, including dentin, bone, and cementum.

As one embodiment, the present invention provides a pharmaceutical composition for preventing or treating dental diseases, comprising CPNE4 protein or a polynucleotide encoding thereof as an active ingredient. In the present invention, the dental disease may include dentin-pulp disease and/or periodontal disease. For example, the present invention can provide a pharmaceutical composition for preventing or treating dentin-pulp disease and/or periodontal disease, comprising CPNE4 protein or a polynucleotide encoding thereof. "CPNE4", which is included as an active ingredient in the composition of the present invention, is known as a gene belonging to the Copine family, but there is no known function of preventing or treating dentin disease, pulp disease, and periodontal disease. On the other hand, dentin disease or pulp disease in the specification may be referred to as dentin-pulp disease.

To achieve the object of the present invention, as long as the effects of the present invention are achieved, various derived and/or forms of CPNE4 gene and/or protein can be used. In addition to the wild-type gene sequence, a gene in which a part of the nucleotide sequence is artificially modified so that characteristics such as expression in a cell or stability of a protein are advantageous, and a gene in which a part of the sequence is modified naturally or fragments of all of these are included. Modification of the gene sequence may or may not involve modification of the corresponding amino acid. When amino acid modifications are involved, the gene in which such modifications are induced is to encode a protein consisting of amino acid sequences in which one or more amino acids have been substituted, deleted, added, and inserted in the protein encoded thereby. The gene includes mutants, derivatives, alleles, variants and homologs. When the modification of the gene sequence does not involve modification of the amino acid in the protein, there is, for example, degeneracy, and such degeneracy mutants are also included in the gene of the present invention.

Modifications of artificial gene sequences can be made by well-known method to those skilled in the art, for example, site-directed mutagenesis (Kramer et al., 1987), error-prone PCR (Cadwell et al., 1992), point mutation method (Sambrook et al., 2001), etc.

Proteins, as used herein, can be prepared using methods known in the art. In one embodiment, the method of producing a protein is by using genetic recombination technology. For example, a vector containing a corresponding gene encoding the protein may be expressed in a prokaryotic or eukaryotic cell, an insect cell or a mammalian cell, and then purified and used. The plasmid can be used, for example, by cloning a gene into an expression vector such as pET28b (Novagen) and transferring it to a cell line, followed by purification of the expressed protein, but is not limited thereto. The synthesized protein can be purified separately by a column chromatography including precipitation, dialysis, ion-exchange chromatography, gel-permeation chromatography, HPLC, reverse phase-HPLC, SDS-PAGE for preparation, affinity column using anti-screening protein antibody, etc.

In one embodiment according to the present application, the CPNE4 gene and protein are derived from mammals such as apes, humans, and the like, but are not limited thereto, and may include birds, reptiles, amphibians, or nematodes. Known CPNE4 gene and protein sequences can be used, for example, NM_001289112, NM_130808, NP_001276041, NP_570720, NP_702907, XP_011510708, XP_011510709, XP_011510710, XP_016861182, XP_016861183, XP_016861184, XP_016861185, NM_028719, NM_001357439, NP_001344368, NP_082995, but are not limited thereto.

In one embodiment according to the present invention, the gene described above may be provided in the form of an expression vector operably linked to a promoter to enable expression in cells in which the composition of the present invention is used.

The term "expression vector", as used herein, refers to a recombinant vector capable of expressing a target gene in a host cell, and refers to a genetic construct including essential regulatory elements which are operably linked to express a gene insert. The expression vector includes expression regulatory sequences such as an initiation codon, a stop codon, a promoter, an operator, etc. The initiation and stop codons are generally considered as part of a nucleotide sequence encoding a polypeptide and are necessary to be functional in an individual to whom a genetic construct has been administered, and must be in frame with the coding sequence. The promoter of the vector may be constitutive or inducible.

The term "operably linked", as used herein, refers to a functional linkage between a nucleic acid expression control sequence and a nucleotide sequence encoding a target protein or RNA in such a manner as to allow general functions. For example, a promoter may be operably linked to a nucleotide sequence encoding a protein or RNA to influence the expression of the coding sequence. The operable linkage to the expression vector may be prepared by using a recombinant genetic technique well known in the art, and site-specific DNA cleavage and ligation may be carried out by using enzymes generally known in the art.

Figure 2A:
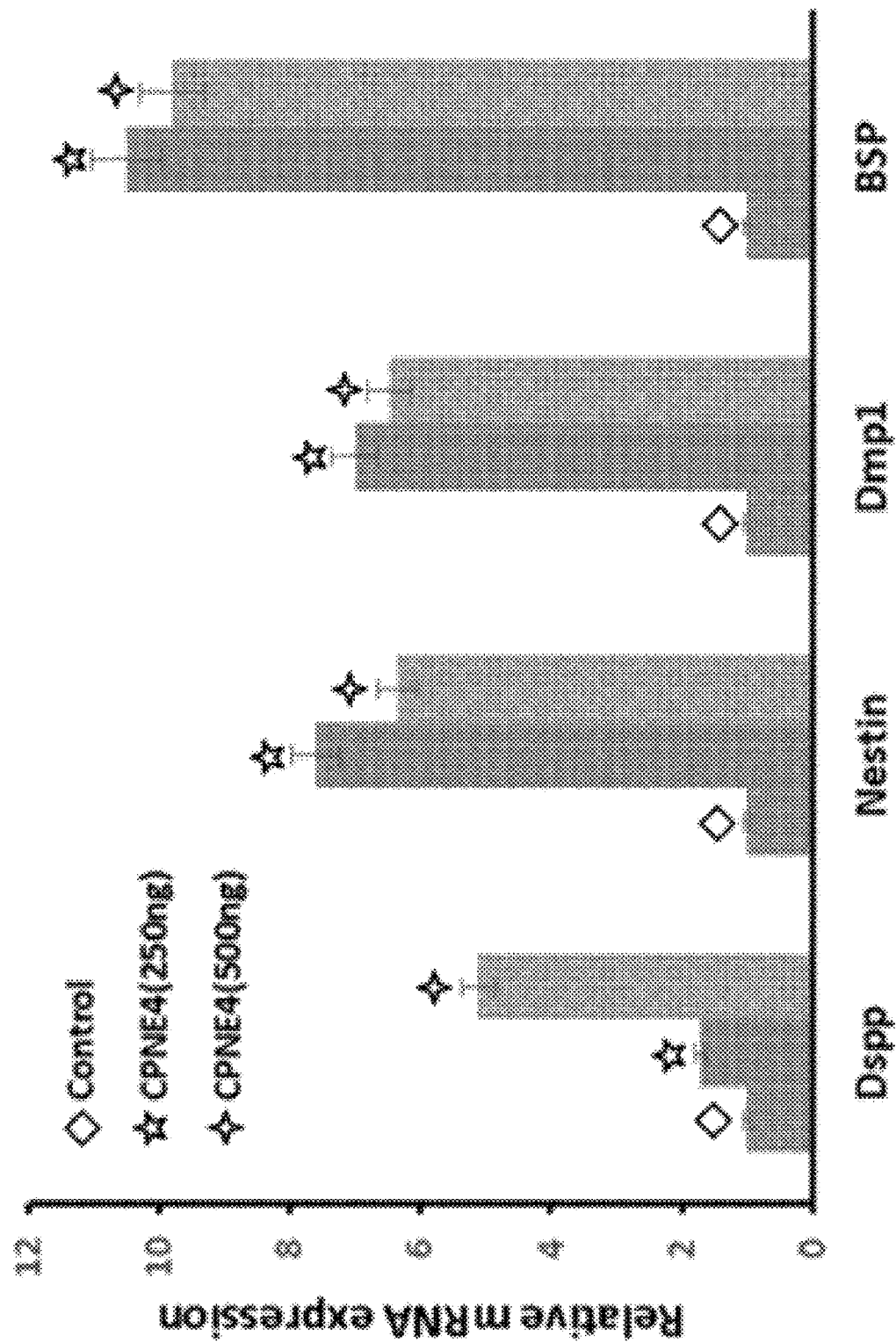
FIG. 2A is a graph showing the results of comparing the expression levels of Dspp and NESTIN, which are the odontoblast differentiation marker genes, and the expression levels of DMP1 and BSP, which are osteoblast and odontoblast differentiation marker gene, in human dental pulp cells (hDPCs) treated with the CPNE4 protein.

According to an embodiment of the present invention, the effect of CPNE4 protein on the expression level of the dentin sialophosphoprotein (Dspp) gene and the NESTIN gene, which are osteoblast differentiation marker genes, in human pulp cells (hDPCs) was confirmed. As a result, the mRNA level of the Dspp gene, which is an osteoblast differentiation marker gene measured in human pulp cells, treated with CPNE4 protein was increased by about 2 to 6 times compared to the mRNA level of the Dspp gene with non-treated with CPNE4(control). In addition, the group treated with CPNE4 protein confirmed that the mRNA level of the NESTIN gene was increased by about 6 to 7.8 times compared to the control group (FIG. 2A).

Figure 2B:
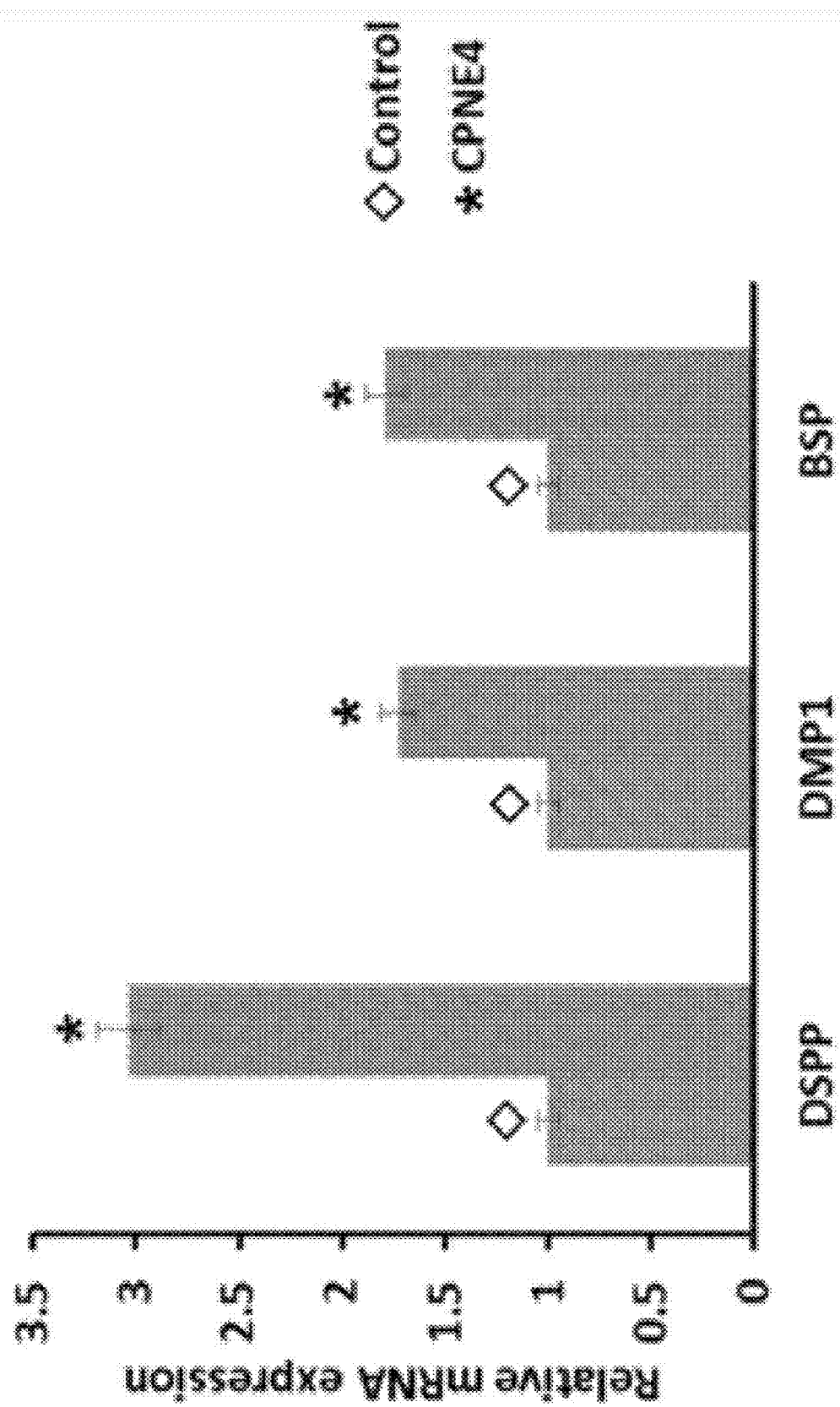
FIG. 2B is a graph showing the results of comparing the expression levels of Dspp, which is the odontoblast differentiation marker gene, and the expression levels of DMP1 and BSP, which are osteoblast and odontoblast differentiation marker gene, in human bone marrow-derived mesenchymal stem cells (hBMSCs) treated with the CPNE4 protein.

In addition, the effect of CPNE4 protein on the expression level of dentin sialophosphoprotein (Dspp) gene, a marker of the odontoblast differentiation marker, in non-dental origin human bone marrow mesenchymal stem cells (hBMSCs) Was verified. As a result, compared to the mRNA level of the Dspp gene, which is a marker for differentiation of the odontoblast differentiated from human bone marrow mesenchymal stem cells (control), which is not treated with CPNE4 protein, the Dspp gene is expressed in human bone marrow mesenchymal stem cells treated with CPNE4 protein. It was confirmed that the mRNA level was increased by about 3 times (FIG. 2B).

It has been reported so far that when the mRNA expression level of the Dspp gene or the NESTIN gene is increased, it is known that the blast cell differentiation and dentin regeneration are promoted, so the CPNE4 protein showing the effect of increasing the mRNA level of the Dspp gene and the NESTIN gene is It was found that it exhibits the effect of promoting the dentin cell differentiation and dentin regeneration.

In addition, the effect of CPNE4 protein on the expression levels of the DMP1 (dentin matrix protein 1) and BSP (Bone sialoprotein) genes, which are the bone and/or cementum differentiation marker genes, was verified. As a result, the mRNA level of the DMP1 gene in human pulp cells treated with CPNE4 protein, compared to the mRNA level of the DMP1 gene, a marker of osteoblast differentiation and/or leukocyte differentiation measured in human pulp cells (control) without CPNE4 protein treatment It was confirmed that the level increased by 6 times or more. In addition, the group treated with CPNE4 protein confirmed that the mRNA level of the BSP gene was increased by about 10 times or more compared to the control group (FIG. 2A).

In addition, the bone marrow and/or cementum differentiation marker genes DMP1 (dentin matrix protein 1) and BSP (Bone sialoprotein) genes in human bone marrow mesenchymal stem cells (hBMSCs) whose CPNE4 protein is of non-dental origin The effect on the expression level was verified. As a result, human bone marrow mesenchymal stem cells treated with CPNE4 protein compared to the mRNA level of the DMP1 gene, a bone marrow and/or white hair cell differentiation marker, measured in human bone marrow mesenchymal stem cells (control) without CPNE4 protein treatment. It was confirmed that the mRNA levels of the DMP1 gene and the BSP gene were increased by about 1.7 times (FIG. 2B).

When the mRNA expression levels of the DMP1 and BSP genes are increased, it is known that the differentiation of osteoblast and/or cementoblast and regeneration of bone and/or cementoblast are promoted, indicating an effect of increasing the mRNA levels of the DMP1 and BSP genes. CPNE4 protein was found to have the effect of promoting the differentiation of bone and/or cementoblast, and bone and/or Cementum regeneration.

As described above, CPNE4, according to the present disclosure, promotes the differentiation of odontoblast, osteoblast, and/or cementoblast in human pulp cells of dental origin. In addition, human dental pulp stem cells (hDPSC), which can be separated from human wisdom teeth, are generally mixed with human pulp cells, and are capable of differentiating into odontoblast, osteoblast, and/or cementoblast. It can be seen that CPNE4, according to the present application, may exhibit an effect of promoting differentiation of human pulp stem cells into odontoblast, osteoblast, and/or cementoblast.

Mesenchymal (dental origin) stem cells, as used herein, refer to stem cells (partial) that are affected by alveolar epithelial cells, and stems distributed in the inner dimension of teeth and tissues around the teeth as ectomesenchyme origin. Cells, such as dental pulp stem cells (DPSC), stem cells from exfoliated deciduous teeth (SHED), periodontal ligament stem cells (PDLSC), apical papillary stems Five are known: stem cells from the apical papilla (SCAP), and dental follicle precursor cells (DFPC).

In addition, CPNE4, according to the present disclosure, promotes differentiation from non-dental origin human bone marrow mesenchymal stem cells to odontoblast, osteoblast, and/or cementoblast. Accordingly, the composition and method comprising CPNE4, according to the present application, has an advantage that non-systemic stem cells, which are readily available, can be differentiated into odontoblast, osteoblast, and/or cementoblast. Until now, most studies on dentin-pulp regeneration and odontoblast differentiation induction and bone/cementum regeneration and induction of osteoblast/cementoblast differentiation have been conducted using dental mesenchymal stem cells. It is a mesenchymal stem cell that has already exchanged signals with the dental epithelium. However, if non-dental mesenchymal stem cells can be used according to the present application, dental mesenchymal stem cells that receive these individual induction signals in dentin-pulp regeneration and induction of odontoblast differentiation and bone/cementum regeneration and osteoblast/cementoblast differentiation, of course even non-dental mesenchymal stem cells can be used, so the types and ranges of available stem cells will be broader, thus increasing the advantages and conveniences in clinical application to real people. In addition, the fact that non-dental mesenchymal stem cells can differentiate into odontoblast, osteoblast, and/or cementoblast can be importantly used to understand the fundamental mechanism of differentiation from mesenchymal stem cells to odontoblast, osteoblast, and/or cementoblast.

The non-dental mesenchymal stem cells of the present application include the concept of stem cells originating from tissues other than the dental tissue in line with the same as the dental mesenchymal stem cells. It may include all stem cells that have not received. For example, it does not originate from the internal dimension of the tooth and the tissue surrounding the tooth, and refers to the following mesenchymal stem cells. Mesenchymal stem cell (MSC) is a stem cell isolated from umbilical cord blood, fat, bone marrow, blood, dermis or periosteum, and differentiates into various cells such as adipocytes, chondrocytes, and bone cells. This refers to a pluripotent or multipotent cell that can. In addition, mesenchymal stem cells are characterized by being able to be engrafted effectively in allogeneic or heterogeneous recipients without the use of immunosuppressive agents.

Figure 13:
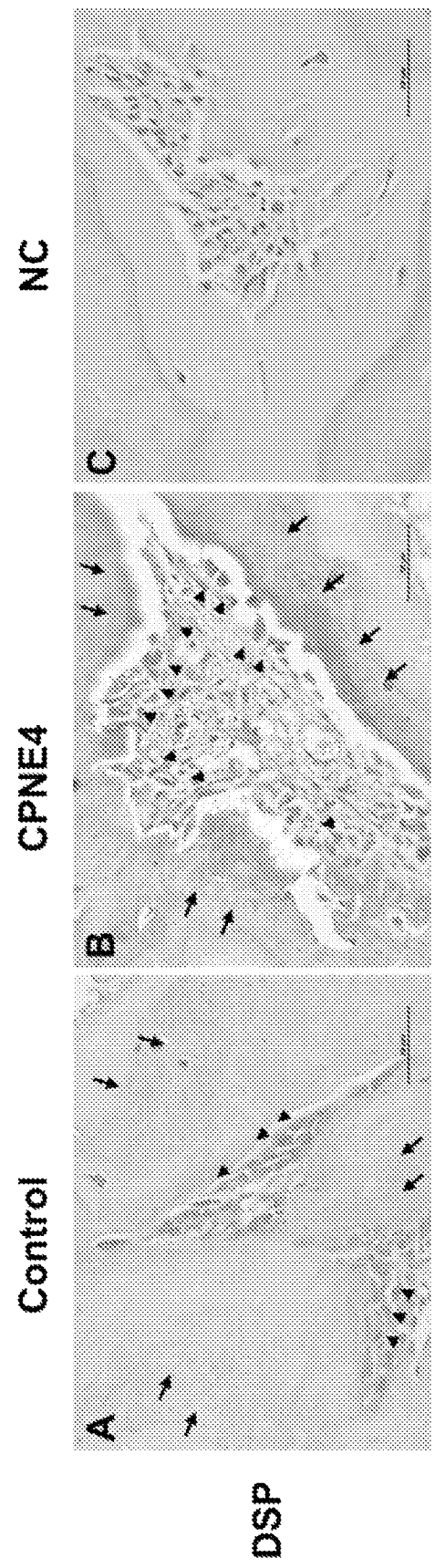
FIG. 13 shows immunostaining images showing the immunohistochemical analysis of the expression level of DSP, odontoblast differentiation marker gene, using immunostaining method, in hard tissue newly formed using human dental pulp cells (hDPCs) for 12 weeks in vivo, in which A shows the results of transplanting the implant prepared by mixing hDPCs and 100 mg HA/TCP in a 0.5% fibrin gel in a mouse with a compromised immune system for 12 weeks, in which B shows the results of transplanting the implant prepared by mixing hDPCs 100 mg HA/TCP, and 5 µg CPNE4 protein in a 0.5% fibrin gel in a mouse with a compromised immune system for 12 weeks. A and B are immunostained of the formed hard tissue using an anti-DSP antibody. C is a negative control of immunohistochemical analysis treated only with secondary antibodies. Arrows in A and B indicate the expression of DSP in newly formed calcified tissue. The scale bar is 50 µm.

In addition, an implant containing CPNE4 protein was prepared with human pulp cells, and the implant was implanted into the subcutaneous tissue of a mouse with an impaired immune system, and after 6 or 12 weeks, the transplanted tissue was analyzed. As a result, in vivo dentin-pulp tissue, the most similar form of dentin-pulp-like tissue is formed, bone-like tissue in the form most similar to in vivo bone tissue is formed, the level of collagen formation increases and newly formed calcified. It was confirmed that the hard tissue of the form in which the collagen fiber bundle was inserted into the tissue by horizontal or inclined travel was observed, and that the expression level of the DSP, a specific differentiation marker gene, was increased (FIGS. 3 to 7, and 9 to 9). FIG. 13).

Figure 8:
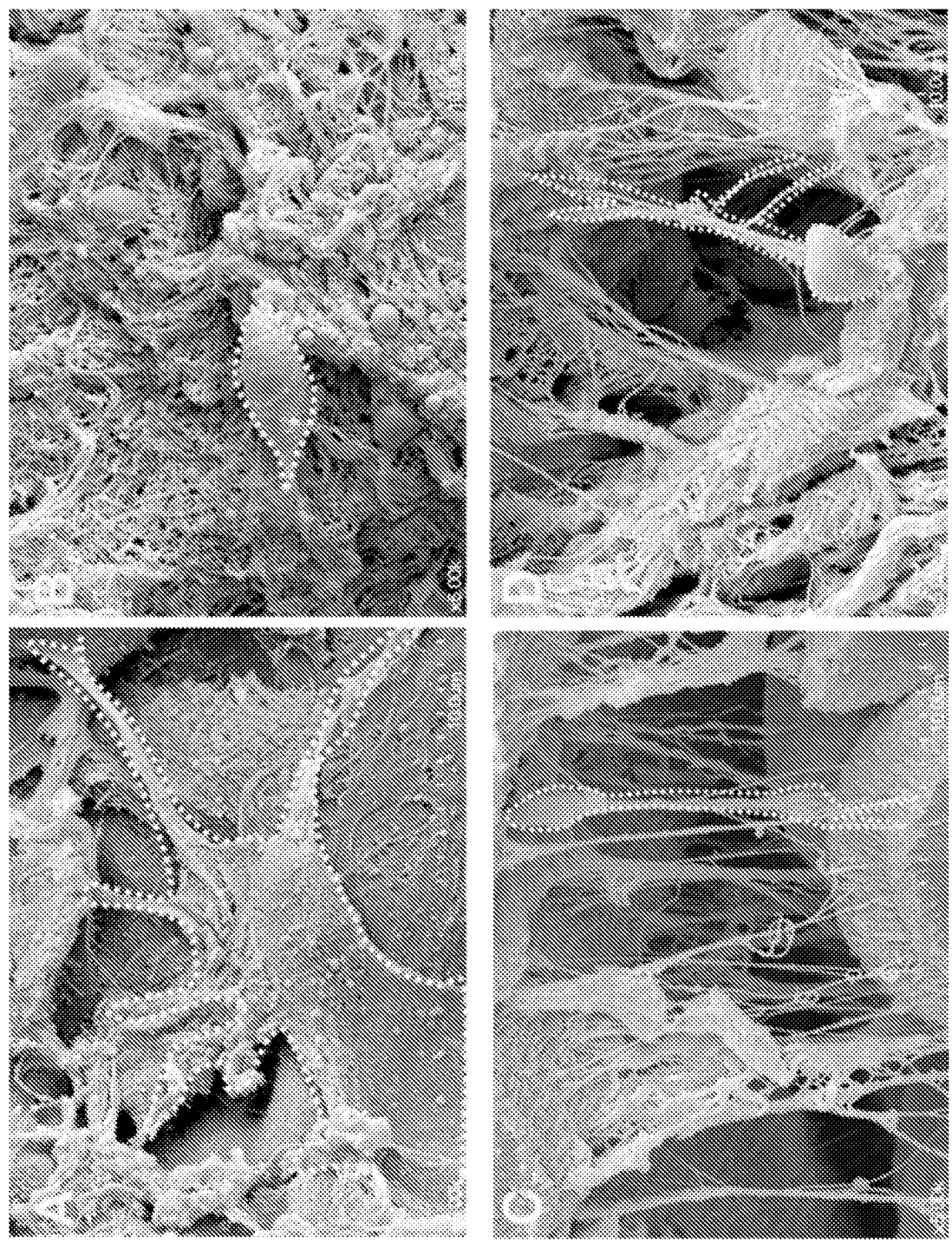
FIG. 8 shows an SEM image showing the analysis of newly formed hard tissue using human pulp cells (hDPCs) for 6 weeks in vivo by a scanning electron microscope (SEM), in which A and B show the results of transplantation of a control implant prepared by mixing hDPCs and 100 mg HA/TCP in a 0.5% fibrin gel for 6 weeks in a mouse with a compromised immune system, and in which C and D show the results of transplantation of implant prepared by mixing hDPCs, 100 mg HA/TCP, and 5 µg CPNE4 protein in a 0.5% fibrin gel for 6 weeks in a mouse with a compromised immune system, respectively. The scale bar is 10 µm.

In addition, as a result of analyzing the shape of the transplanted tissue through a scanning electron microscope, it was confirmed that the odontoblast-like cells were observed along the formed hard tissue, and that the odontoblast were also extended toward the formed hard tissue (FIG. 8).

As described above, when CPNE4 protein is transplanted in vivo with human dental pulp cells, it can promote the formation of dentin/dental pulp-like tissue. Therefore, the CPNE4 protein may be used as an active ingredient in a pharmaceutical composition for treating dentin-dental pulp disease caused by damage to the pulp tissue. In addition, when the CPNE4 protein is transplanted in vivo with human dental pulp cells, the human dental pulp cells can promote the formation of bone-like tissues. Therefore, the CPNE4 protein may be used as an active ingredient in a pharmaceutical composition for the treatment of periodontal disease-causing bone and/or cementum damage.

Accordingly, the pharmaceutical composition for preventing or treating dentin-dental pulp disease and/or periodontal disease comprising the CPNE4 protein or its gene of the present invention has been found that it can promote regeneration of hard tissue and/or pulp tissue including dentin, bone, and cementum, and have the effect of preventing or treating effect of dentin-dental pulp disease and/or periodontal disease. The pharmaceutical composition of the present invention exhibiting this effect has not been reported at all so far, and was first developed by the inventor. The term "dentin-dental pulp diseases", as used herein, refer to all diseases caused by damaged dental pulp tissue and dentin linked to the dental pulp due to damage to the dentin and dental pulp tissues.

In the present invention, the dentin-dental pulp diseases are not particularly limited, as long as the pharmaceutical composition of the present invention exhibits the therapeutic effects on the diseases, and the dentin or dental pulp diseases may include, for example, dentin hypersensitivity, pulp hyperemia, pulpitis, pulp degeneration, pulp necrosis, gangrenous pulp, etc.

The term "periodontal disease", as used herein, also referred to as chronic periodontitis, refers to a disease that infects the periodontal ligament and adjacent tissues by infection of bacteria in the gap between the gingiva and the teeth, depending on the severity of the disease it is divided into gingivitis or periodontitis. During the onset of periodontal disease, inflammation progresses, and more tissues are damaged to form a periodontal pocket. It is known when periodontitis gets worse, and the periodontal pocket becomes deeper the periodontal pocket causes inflammation of periodontal ligament and finally cause bone loss.

In the present invention, the periodontal diseases are not particularly limited, as long as the pharmaceutical composition of the present invention exhibits the therapeutic effects on the diseases, and the dentin or dental pulp diseases may include, for example, gingivitis, periodontitis, periodontal pocket or periodontal abscess, etc.

The term "preventing", as used herein, means all actions by which the dentin-dental pulp disease and/or occurrence of dentin-dental pulp diseases is restrained or retarded by administration of the pharmaceutical composition of the present invention.

The term "treating", as used herein, means all actions by which dentin dental pulp diseases are treated by promoting regeneration of dentin or dental pulp by administering the pharmaceutical composition to a subject in need of treatment of dentin-dental pulp diseases and/or all actions which are carried out the treatment of periodontal disease by promoting regeneration of bone and cementum.

The pharmaceutical composition of the present invention may be prepared in the form of a pharmaceutical composition for treating dentin-dental pulp diseases and/or periodontal diseases further including, an appropriate carrier (natural or non-natural carrier), excipient, or diluent commonly used in the preparation of pharmaceutical compositions. Notably, the pharmaceutical composition may be formulated according to a standard method in the form of a sterile injectable solution that may be administered to dentin or dentin-dental pulp diseases and/or periodontal diseases-induced site. In the present invention, the carrier, excipient, and diluent which may be included in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, mineral oils, collagen, etc. Upon formulation, commonly used diluents or excipients such as a filler, an extender, a binder, a wetting agent, a disintegrant, a surfactant, etc. may be used. In particular, a sterilized aqueous solution, a non-aqueous solvent, a suspension, an emulsion, a freeze-dried preparation, a suppository, an ointment (e.g., pulp liner, etc.) may be included. As non-aqueous solvents or suspensions, propylene glycol, polyethylene glycol, plant oils such as olive oil, injectable esters such as ethyl oleate, etc. may be used. As a base of the suppositories, witepsol, Macrogol, Tween 61, cacao butter, laurin fat, glycerogelatin, etc. may be used.

A content of CPNE4 protein in the pharmaceutical composition of the present invention is not particularly limited, but CPNE4 protein may be included in an amount of 0.0001% by weight to 50%, more preferably, 0.01% by weight to 20% by weight, based on the total eight of the final composition.

The pharmaceutical composition of the present invention may be administered in a pharmaceutically effective amount. The term "pharmaceutically effective amount", as used herein, refers to an amount sufficient to treat or prevent diseases, at a reasonable benefit/risk ratio applicable to any medical treatment or prevention. An effective dosage level may be determined depending on factors including the severity of the disease, drug activity, a patient's age, body weight, health conditions, sex, sensitivity to the drug, administration time, administration route, and excretion rate of the composition of the present invention, duration of treatment, drugs blended with or co-administered with the composition of the present invention, and other factors known in the medical field. The pharmaceutical composition of the present invention may be administered individually or in combination with a known pharmaceutical composition for treating dentin-dental pulp diseases and/or periodontal diseases. It is essential to administer the composition in a minimum amount that may exhibit a maximum effect without causing side effects, because of all the above-described factors.

An administration dose of the pharmaceutical composition of the present invention may be determined by those skilled in the art, because of the purpose of use, severity of the disease, a patient's age, body weight, sex, and medical history, a kind of a material used as an active ingredient, etc. For example, the pharmaceutical composition of the present invention may be administered at a dose of about 0.1 ng/kg to about 100 mg/kg. Preferably, about 1 ng/kg to about 10 mg/kg per adult and administration frequency of the composition of the present invention is not particularly limited. However, the composition may be administered once a day or several times a day in divided doses. The administration dose does not limit the scope of the present invention in any aspect.

In still another aspect, the present invention provides a method of preventing or treating dentin-dental pulp diseases and/or periodontal disease, the method including administering the pharmaceutically effective amount of the pharmaceutical composition to a human or a subject having dentin-dental pulp diseases.

The term "subject, as used herein, may include mammals including rats, livestock, etc. in need of treatment of dentin-dental pulp diseases and/or periodontal diseases without limitation, but humans can be excluded from the subjects having the above diseases.

The pharmaceutical composition of the present invention may be administered via any general route, as long as the pharmaceutical composition can reach a target tissue. The pharmaceutical composition may be administered, but is not particularly limited to, via intraoral administration, intraoral injection, etc., depending on the purpose.

In still another aspect, the present invention provides the use of a composition comprising CPNE4 protein or the polynucleotide encoding thereof for the prevention or treatment of dentin-dental disease and/or periodontal disease.

In still another aspect, the present invention provides a composition comprising CPNE4 protein or a polynucleotide encoding thereof for promoting regeneration of hard tissue including dentin, bone and cementum, and/or pulp tissue.

As described above, the CPNE4 protein not only promotes differentiation or odontoblast and dentin regeneration, but also promotes differentiation of osteoblast and cementoblast, and regeneration of bone and cementum. Therefore, it can be used as an active ingredient of the composition for promoting regeneration of hard tissue, including dentin, bone and cementum, and/or pulp tissue. In one embodiment, the composition for promoting regeneration of the present invention may be used as a cell therapy product for regeneration of hard tissue, including dentin, bone and cementum, and/or pulp tissue.

The term "cell therapy product", as used herein, means a drug used to proliferate and screen autologous, allogenic, xenogenic cells in vitro to restore the function of cells and tissues or a drug used for treatment, diagnosis, and prevention through actions such as changing the biological properties of cells by other methods. The US has been managing cell therapy products as pharmaceuticals since 1993, and Korea since 2002. Such cell therapy products include, but are not limited to, stem cell therapy for tissue regeneration or recovery of specific organ functions.

In still another aspect, the present inventive concepts may also provide a method of promoting regeneration of hard tissue including dentin, bone, and cementum and/or dental pulp tissue, the method including administering the composition for promoting regeneration of hard tissue including dentin, bone, and cementum and/or dental pulp tissue to a human or a subject. The term "subject" is as described above.

In still another aspect, the present inventive concept may also provide a use of a composition comprising CPNE4 protein or a polynucleotide encoding thereof for promoting regeneration of hard tissue including dentin, bone, and cementum, and/or pulp tissue.

In still another aspect, the present invention provides a composition comprising CPNE4 protein or a polynucleotide encoding thereof for promoting regeneration of hard tissue including dentin, bone and cementum, and/or pulp tissue.

As described above, the CPNE4 protein not only promotes differentiation or odontoblast and dentin regeneration, but also promotes differentiation of osteoblast and cementoblast, and regeneration of bone and cementum. Therefore, it can be used as an active ingredient of the composition for promoting regeneration of hard tissue, including dentin, bone and cementum, and/or pulp tissue.

In still another aspect, the present inventive concept may also provide a use of a composition comprising CPNE4 protein or a polynucleotide encoding thereof for promoting regeneration of hard tissue including dentin, bone, and cementum, and/or pulp tissue.

In still another aspect, the present invention provides a quasi-drug composition for preventing or alleviating of dentin-dental disease and/or periodontal disease comprising CPNE4 protein or a polynucleotide encoding thereof.

The term "alleviating", as used herein, means all actions that at least reduce a parameter related to the conditions to be treated, for example, the degree of symptom.

In the present invention, the alleviating is to be interpreted as all actions by which symptoms of dentin-dental pulp disease and/or periodontal disease have taken a turn for the better or been modified favorably by promoting regeneration of dentin-dental pulp or symptoms of periodontal diseases have taken a turn for the better or been modified favorably by promoting regeneration of bone and/or cementum by administering the composition of the present invention comprising the CPNE4 protein or a polynucleotide encoding thereof as an active ingredient to a subject in need of treatment of dentin or dental pulp disease and/or periodontal disease.

The term "quasi-drug", as used herein, refers to an article having a milder action than drugs, among articles being used for diagnosis, treatment, improvement, alleviation, handling, or prevention of human or animal diseases. For example, according to Pharmaceutical Affairs Law, the quasi-drugs are those, excluding articles used as drugs, including articles made from fiber or rubber which are used to treat or prevent human or animal diseases, articles, other than a tool or a machine, or an analog thereof, which have a mild action on or have no direct influence on the human body, and articles which are used for disinfection or pest control for the prevention of infectious diseases.

In the present invention, a kind of formulation of the quasi-drug composition, including the CPNE4 protein of a polynucleotide encoding thereof, is not particularly limited. However, the quasi-drug composition may be, for example, oral antiseptic mouthwashes, oral hygiene products, toothpastes, floss, oral ointments, etc.

In still another aspect, the present invention provides a health functional food composition for preventing or alleviating dentin-dental pulp diseases and/or periodontal diseases, comprising the CPNE4 protein of a polynucleotide encoding thereof.

The term "food", as used herein, includes meats, sausages, breads, chocolates, candies, snacks, confectionery, pizzas, ramen noodles, other noodles, gums, dairy products including ice-creams, various soups, beverages, teas, drinks, alcoholic beverages, and vitamin complexes, health functional foods, health foods, etc., and the food includes all foods in the ordinary acceptation of the term.

The term "functional food", as used herein, is the term identical to the food for special health use (FoSHU), and refers to a food having high medical, medicinal effects, which is processed to exhibit the biologically modulating function efficiently as well as to supply nutrients. Here, the term "functional" indicates a beneficial effect for human health, such as the regulation of nutrients for the structure and function of the human body, physiological action, etc. The food of the present invention may be prepared according to a method commonly employed in the art, and raw materials and ingredients commonly used in the art may be added upon preparing the food. In addition, a formulation of the food is not limited, as long as the formulation is accepted as a food. The food composition of the present invention may be prepared as a variety of formulations. Since the food is used as raw materials, unlike general drugs, the food composition lacks side effects which may occur when a drug is taken for an extended period, and may have excellent portability. Therefore, the food of the present invention may be taken as a supplement for enhancing the effects of preventing or alleviating dentin-dental pulp diseases and/or periodontal diseases.

The health food means food is having effects of actively maintaining or promoting health conditions, as compared with general foods, and the health supplement food means a food for supplementing health. If necessary, the health functional food, health food, and health supplement food may be interchangeably used.

Specifically, the health functional food is a food prepared by adding the CPNE4 protein of the present invention to food materials such as beverages, teas, spices, gums, confectionery, etc., or prepared as a capsule, a powder, a suspension, etc. The functional health food means that it takes a specific effect on health when consumed, but unlike general drugs, the health functional food has an advantage of having no side effects that may occur when a drug is taken for a long time, because it uses a food as a raw material.

Since the food composition of the present invention is routinely ingested, the food composition is expected to show high efficacy on prevention or improvement of dentin-dental pulp diseases and/or periodontal diseases. Thus, it may be very usefully applied.

The food composition may further include a physiologically acceptable carrier. A kind of the carrier is not particularly limited. Any carrier may be used, as long as it is commonly used in the art.

Further, the food composition may include additional ingredients that are commonly used in food compositions to improve smell, taste, vision, etc. For example, the food composition may include vitamins A, C, D, E, B1, B2, B6, B12, niacin, biotin, folate, pantothenic acid, etc. Additionally, the food composition may also include minerals such as Zn, Fe, Ca, Cr, Mg, Mn, Cu, etc. Additionally, the food composition may also include amino acids such as lysine, tryptophan, cysteine, valine, etc. Additionally, the food composition may also include food additives, such as preservatives (potassium sorbate, sodium benzoate, salicylic acid, sodium dehydroacetate, etc.), disinfectants (bleaching powder, higher bleaching powder, sodium hypochlorite, etc.), antioxidants (butyl hydroxyanisole (BHA), butylhydroxytoluene (BHT), etc.), coloring agents (tar color, etc.), color-developing agents (sodium nitrite, etc.), bleaching agents (sodium sulfite), seasonings (monosodium glutamate (MSG), etc.), sweeteners (dulcin, cyclamate, saccharin, sodium, etc.), flavors (vanillin, lactones, etc.), swelling agents (alum, potassium D-bitartrate, etc.), fortifiers, emulsifiers, thickeners (adhesive pastes), film-forming agents, gum base agents, antifoaming agents, solvents, improvers, etc. The additives may be selected and used in an appropriate amount according to the food types.

The CPNE4 protein of the present invention may be added as it is, or may be used in conjunction with other foods or food ingredients according to a standard method, or may be used appropriately according to a standard method. Mixing amounts of the active ingredient may be suitably determined depending upon the purpose of use (prophylactic, health or treatment). Generally, upon production of a food or a beverage, the food composition of the present invention may be added in an amount of 50 parts by weight or less, precisely 20 parts by weight or less, based on the total weight of the food or the beverage. However, when prolonged intake is intended for health and hygiene, the food composition may be included in an amount below the above range. In addition, since there is no safety problem, the active ingredient may be used in an amount above the high range.

The food composition of the present invention may be used as, for example, a health beverage composition. In this case, the health beverage composition may further include various flavors or natural carbohydrates, as in common beverages. The natural carbohydrates may include monosaccharides such as glucose and fructose; disaccharides such as maltose and sucrose; polysaccharides such as dextrin and cyclodextrin; and sugar alcohols such as xylitol, sorbitol, and erythritol. The sweeteners may be natural sweeteners such as thaumatin or a stevia extract; or synthetic sweeteners such as saccharine or aspartame. The natural carbohydrate may be generally used in an amount of about 0.01 g to 0.04 g, and individually, about 0.02 g to 0.03 g, based on 100 mL of the health beverage composition of the present invention.

In addition, the health beverage composition may include various nutrients, vitamins, minerals, flavors, colorants, pectic acid and salts thereof, alginic acid and salts thereof, organic acids, protective colloidal thickeners, pH modifiers, stabilizers, antiseptics, glycerin, alcohols, carbonating agents, etc. Moreover, the health beverage composition may include the fruit flesh used to prepare natural fruit juices, fruit juice beverages, or vegetable beverages. These ingredients may be used individually or in combination. A proportion of the additives is not critical, but is generally selected from 0.01 parts by weight to 0.1 parts by weight per 100 parts by weight of the health beverage composition of the present invention.

The food composition of the present invention may include the CPNE4 protein of the present invention in a variety of % by weight, as long as it may exhibit the effect of preventing or alleviating dentin-dental pulp diseases and/or periodontal diseases. Specifically, the CPNE4 protein of the present invention may be included in an amount of 0.00001% by weight to 100% by weight or 0.01% by weight to 80% by weight, based on the total weight of the food composition, but is not limited thereto.

In still another aspect, the present invention provides a method of preventing or treating dentin-dental pulp diseases and/or periodontal diseases, the method including administering the composition, including the CPNE4 protein to a subject.

Hereinafter referred to as the present invention will be described in more detail with reference to Examples. However, these examples are for illustrative purposes only, and the scope of the present invention is not intended to be limited by these Examples.

Example 1: Methods and Materials

Example 1-1. Cell Culture and Differentiation

Cells were cultured in humidified air containing 37% about $CO_2$ at 37° C. and used in the experiment. MDPC-23 cells, a mouse odontoblast line, and human bone marrow mesenchymal stem cells (hBMSCs) were used. MDPC-23 cells were provided by Dr. J. E. Nor (University of Michigan, Ann Arbor, Mich.), and human bone marrow mesenchymal stem cells (hBMSCs) were purchased from Lonza (LONZA, Switzerland).

MDPC-23 cells were cultured in Dulbecco's modified Eagle's medium (Invitrogen) supplemented with 10% heat-inactivated bovine serum. The odontoblasts were differentiated for 14 days using a differentiation medium containing 50 mg/ml ascorbic acid and 10 mM beta-glycerophosphate. Human bone marrow mesenchymal stem cells were cultured in a culture of alpha-m ($\alpha$-MEM, Invitrogen) supplemented with 10% heat-inactivated bovine serum. CPNE4 recombinant protein (250 ng/ml, 500 ng/ml) was added and cultured.

Example 1-2. Isolation and Culture of Human Dental Pulp Cells (hDPCs)

Human dental pulp cells (hDPCs) (i.e. human dental pulp derived cells) isolated from wisdom teeth of 10 adults (aged 18-22) at the School of Dentistry, Seoul National University. In detail, all experiments were performed after the approval of the Institutional Review Board and the informed consent from patients. Wisdom teeth were fractured according to a method of Jung H S et al. (J Mol Histol. (2011)) to expose the dental pulps, and dental pulp tissues were separated with forceps. Each of the separated dental pulp tissues was cut into small pieces with a razor blade, put in a 60-mm dish, covered with a coverslip, and then cultured in a Dulbecco's modified Eagle's medium. It has been known that human dental pulp cells can differentiate into odontoblast, osteoblast, cementoblast, and periodontal ligament cells under various conditions (Tissue Eng Part A. 2014 April; 20 (7-8): 1342-51).

Example 1-3. Analysis of Reverse Transcription-Polymerase Chain Reaction (RT-PCR) and Real-Time PCR Total RNA was extracted from mouse odontoblast line MDPC-23 cells, human dental pulp cells (hDPCs), and human bone marrow mesenchymal stem cells (hBMSCs) with TRIzol reagent. 2 μg of the total RNA, 1 μl of reverse transcriptase, and 0.5 μg of oligo (oligo; dT) were used to synthesize cDNA of MPC-23 cells. RT-PCR of synthesized cDNA of MDPC-23 cells was performed using the primers of the mouse in Table 1 below. Polymerase chain reaction was 94° C., 5 minutes; 95° C., 30 seconds; 60° C., 30 seconds; 72° C., 30 seconds were performed under the conditions of repeating 32 cycles. PCR products were analyzed by electrophoresis on a 2% agarose gel.

The synthesized cDNA of human dental pulp cells (hDPCs) and human bone marrow mesenchymal stem cells (hBMSCs) were used in a real-time polymerase chain reaction. The real-time polymerase chain reaction was performed on an ABI PRISM 7500 sequence detection system (Applied Biosystems) and an SYBR GREEN PCR Master Mix (Takara, Japan). The real-time polymerase chain reaction was performed under conditions of 94° C., 1 min; 95° C., 15 sec; 60° C., 34 sec for 40 cycles. Results were analyzed by a comparative cycle threshold (CT) method.

Table 1

<Complete lists of mouse RT-PCR primers>

| Gene | | Primer (5'-3') |
|---|---|---|
| Dspp | forward | ATTCCGGTTCCCCAGTTAGTA (SEQ ID NO: 1) |
| | reverse | CTGTTGCTAGTGGTGCTGTT (SEQ ID NO: 2) |
| Gapdh | forward | AGGTCGGTGTGAACGGATTTG (SEQ ID NO: 3) |
| | reverse | TGTAGACCATGTAGTTGAGGTCA (SEQ ID NO: 4) |

Table 2

<Complete lists of human real time PCR primers>

| Gene | | Primer (5'-3') |
|---|---|---|
| hDSPP | forward | CAACCATAGAGAAAGCAAACGCG (SEQ ID NO: 5) |
| | reverse | TTTCTGTTGCCACTGCTGGGAC (SEQ ID NO: 6) |
| hNESTIN | forward | AGCCCTGACCACTCCAGTTTAG (SEQ ID NO: 7) |
| | reverse | CCCTCTATGGCTGTTTCTTTCTCT (SEQ ID NO: 8) |
| hBSP | forward | GAATGGCCTGTGCTTTCTCAA (SEQ ID NO: 9) |
| | reverse | TCGGATGAGTCACTACTGCCC (SEQ ID NO: 10) |
| hDMP1 | forward | ACAGGCAAATGAAGACCC (SEQ ID NO: 11) |
| | reverse | TTCACTGGCTTGTATGG (SEQ ID NO: 12) |
| hGAPDH | forward | CCATGGAGAAGGCTGGGG (SEQ ID NO: 13) |
| | reverse | CAAAGTTCTCATGGATGACC (SEQ ID NO: 14) |

Example 1-4. In Vivo Transplantation and Histomorphological Analysis

Human dental pulp cells (hDPCs) were isolated and used for in vivo transplantation experiments. Human dental pulp cells ($2\times10^6$) were mixed with 100 mg of hydroxyapatite/tricalcium phosphate (HA/TCP) ceramic powder (Zimmer, USA) alone, or with CPNE4 protein (5 µg, Origene, USA) of the invention with 0.5% fibrin gel respectively, and then the prepared implant transplanted to mice with compromised immune systems (NIH-bg-nu-xid; Harlan Laboratories, Indianapolis, Ind.), and the mice were raised for 6 and 12 weeks.

After that, the sample tissues were harvested and fixed in 4% paraformaldehyde, decalcified in 10% EDTA (pH 7.4), embedded in paraffin, stained with hematoxylin-eosin (H-E) (Vector Labs), or conducted Immunohistochemical analysis. To immunohistochemical analysis, proteins were detected with anti-DSP antibody diluted 1:150 as the primary antigen, and goat anti-rabbit IgG (Vector Labs) labeled with biotin as secondary antigen.

Collagen staining was conducted by using a Masson's Trichrome Stain Kit (Cat. 25088-100) of Polysciences, co.

Quantitative analysis of newly formed hard tissue was analyzed using the LS starter program (OLYMPUS Soft Imaging Solution, Muster, Germany). The proportion of newly formed hard tissue was calculated as the percentage of the area of newly formed hard tissue in the total area.

Example 1-5. Scanning Electron Microscope Analysis

The sample tissues were fixed in 2.5% Glutaraldehyde/0.1 M Cacodylate buffer for 30 minutes and reacted in a solution containing 1% osmium tetroxide in 0.1 M Cacodylate buffer for 1 hour. Then, the sample tissues were quickly dehydrated and dried using ethanol, and then the sample tissues were coated with gold and observed with a scanning electron microscope (S-4700, HITACHI, Tokyo, Japan).

Example 1-6. Statistical Analysis

Statistical analysis was performed using Student's t-test. All statistical analysis is performed by SPSS software ver. 19.0.

Example 2: Experimental Results

Example 2-1. Analysis of CPNE4 Gene Expression Changes During Odontoblast Differentiation Process Proteins such as dentin matrix protein 1 (DMP1) or dentin matrix protein 4 (DMP4), which regulate the differentiation of cells capable of forming hard tissue (eg, odontoblast or osteoblast), can bind calcium (J Biol Chem. 2007 May 25; 282(21):15357-65). The present inventors investigated the protein capable of binding calcium and confirmed that CPNE4 has a domain capable of binding calcium. Accordingly, the effect of CPNE4 on the differentiation of hard tissue-forming cells in the present invention was investigated.

To confirm CPNE4 gene expression during the process of differentiating the odontoblast, RT-PCR was performed by culturing the MDPC-23 cells, which are the blast cell lines, in differentiation medium for 2 weeks, and analyzed the results, and the results are shown in FIG. 1.

FIG. 1 shows the result of confirming the CPNE4 gene expression change during the odontoblast differentiation process through reverse transcriptase chain reaction (RT-PCR). As shown in the FIG. 1, the expression of the CPNE4 gene increased on the 7th day of differentiation and maintained until 10th, and decreased on the 14th day of differentiation.

Example 2-2. The Effect of CPNE4 Protein on the Expression Level of Dspp Gene and NESTIN Gene, which are the Markers of Odontoblast Differentiation The Dspp (Dentin sialophosphoprotein) gene and NESTIN gene are used as a marker for odontoblast cell differentiation and is known as an essential gene for dentin calcification. Therefore, it was confirmed that the CPNE4 protein of the present invention has an effect of promoting the expression of the Dspp gene and NESTIN gene, which is odontoblast differentiation marker gene, and promoting odontoblast and the formation of dentin.

The human dental pulp cells (hDPCs) cultured in Example 1-2 were treated with the CPNE4 protein (concentration of 250 ng/ml, 500 ng/ml, respectively), and cultured for 48 hours. Then, levels of an odontoblast differentiation marker Dspp gene and NESTIN gene measured by quantitative real-time PCR (see the method of Example 1-3). In this case, human dental pulp cells that were not treated with the CPNE4 protein of the present invention were used as a control. The results are shown in FIG. 2A.

FIG. 2A is a graph showing the results of comparing the expression levels of Dspp and NESTIN, which are the blast cell differentiation marker genes, and the expression levels of DMP1 and BSP, which are osteoblast and Cementoblast differentiation marker gene, in human pulp cells (hDPCs) treated with CPNE4 protein.

As shown in FIG. 2A, the mRNA expression level of the Dspp gene of the CPNE4 protein-treated group increased concentration-dependently on the CPNE4 protein compared to the control group, and was confirmed to be increased by about 2 to 6 times or more compared to the control group. In addition, in the group treated with CPNE4 protein, it can be confirmed that the expression level of the NESTIN gene was increased by about 6 to 7.8 times compared to the control group.

And, the human bone marrow mesenchymal stem cells (hBMSCs) cultured through the method of Example 1-1 were treated with 250 ng/ml of CPNE4 protein, cultured for 48 hours, and then expression level or Dspp gene, an odontoblast differentiation marker was measured by quantitative real-time PCR (see the method of Examples 1-3). At this time, human bone marrow mesenchymal stem cells not treated with CPNE4 protein were used as a control. The results are shown in FIG. 2b.

FIG. 2B is a graph showing the results of comparing the expression level of the Dspp gene, odontoblast differentiation marker gene with DMP1 gene and BSP gene, bone, and cementum differentiation marker gene, in human-derived mesenchymal stem cells (hBMSCs) treated with the CPNE4 protein of the present invention.

As shown in FIG. 2a, it was confirmed that the mRNA expression level of the Dspp gene in the group treated with the CPNE4 protein was increased by about 3 times compared to the control. Accordingly, it was confirmed that the CPNE4 protein could exhibit the effect of promoting the regeneration of dentin and/or dental pulp tissue by promoting the differentiation of non-dental human bone marrow mesenchymal stem cells into odontoblast.

Since the Dspp gene or the NESTIN gene is known as a gene involved in the process of blast cell differentiation and dentin calcification, the CPNE4 protein provided by the present invention or a dentin-memory disease and/or periodontal disease comprising the gene The pharmaceutical composition was analyzed to have an effect of promoting dentin regeneration.

Dspp gene or the NESTIN gene is known as a gene involved in the process of odontoblast differentiation, and dentin calcification, the pharmaceutical composition comprising the CPNE4 protein provided by the present invention or a polynucleotide encoding thereof was analyzed to have an effect of promoting dentin regeneration.

Example 2-3. Effect of CPNE4 Protein on the Expression Levels of DMP1 and BSP Genes, which are Markers of Osteoblast and Cementoblast Differentiation Markers The DMP1 gene and BSP gene are used as markers for differentiating osteoblast and cementoblast, and are known as essential genes for calcification of bone and cementum (International Journal of Oral Science (2012) 4, 119-128). Therefore, in order to confirm the effect of the CPNE4 protein of the present invention on the expression of the DMP1 and BSP genes, which are the markers of bone and cementoblast differentiation, the CPNE4 protein was treated in human pulp cells (hDPCs) in a concentration-dependent manner. And, DMP1 gene and BSP gene expression levels were measured by real-time PCR. In addition, after treating CPNE4 protein in human bone marrow mesenchymal stem cells (hBMSCs), DMP1 and BSP gene expression levels were measured by real-time PCR.

Roughly, similar to Example 2-2, except using primers, similar methods were performed, the effect of CPNE4 protein on DMP1 and BSP gene expression levels in human pulp cells and human bone marrow mesenchymal stem cells was measured, and the results are shown in FIGS. 2a and 2b, respectively. At this time, human pulp cells not treated with CPNE4 protein and human bone marrow mesenchymal stem cells not treated with CPNE4 protein were used as controls.

As shown in FIG. 2a, the group treated with the CPNE4 protein of the present invention, it can be seen that the DMP1 gene expression increased by about 6 times or more, and the BSP gene expression increased by about 10 times or more compared to the control.

As shown in FIG. 2b, the group treated with the CPNE4 protein of the present invention, and it can be seen that the DMP1 gene and BSP gene expression increased by about 1.7 times or more. Accordingly, it was confirmed that the CPNE4 protein could exhibit the effect of promoting the regeneration of bone and/or cementum by promoting the differentiation of non-dental human bone marrow mesenchymal stem cells into odontoblast.

As DMP1 and BSP gene are used as a marker for differentiating osteoblasts and cementoblasts and are known as a gene involved in the process of calcification of bone and cementum, it was analyzed that the pharmaceutical composition for preventing or treating dentin-pulp disease and/or periodontal disease comprising the CPNE4 protein and a polynucleotide encoding thereof provided in the present invention would have an effect of promoting regeneration of bone and cementum.

Example 2-4. Hard Tissue Formation of Human Dental Pulp Cells (hDPCs) by CPNE4 Protein In Vivo for 6 Weeks (1) Histomorphological Analysis FIG. 2A, based on the results of the in vitro experiments, in order to confirm the effect of CPNE4 protein of the present invention on hard tissue formation in vivo, described in Examples 1-4 above As described, human dental pulp cells (hDPCs) and 100 mg of hydroxyapatite/tricalcium phosphate (HA/TCP) were mixed with 0.5 µg fibrin gel, respectively, with 5 µg of CPNE4 protein to prepare an implant. The implant was transplanted into the subcutaneous tissue of a mouse with a compromised immune system. At this time, as a control, a transplanted implant containing no CPNE4 protein of the present invention was used. After 6 weeks of transplantation, a sample was taken, and then the newly formed hard tissue was quantitatively analyzed using the LS starter program, and the results are shown in FIG. 3.

Figure 3:
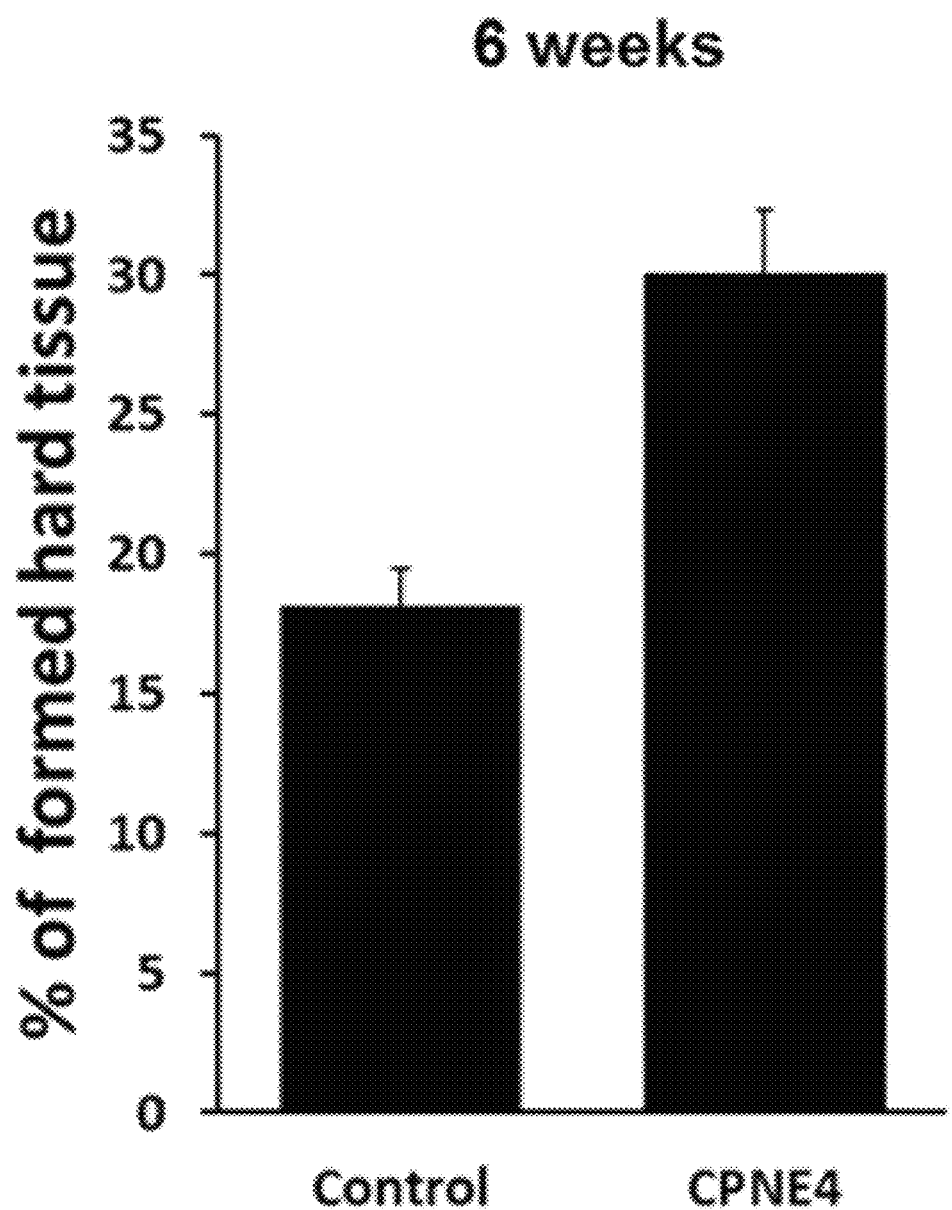
FIG. 3 shows the results of measuring the amount of newly formed hard tissue using human dental pulp cells (hDPCs) for 6 weeks in vivo.

FIG. 3 shows the results of measuring the amount of newly formed hard tissue using human dental pulp cells (hDPCs) for 6 weeks in vivo. As shown in FIG. 3, the ratio of hard tissue formation after 6 weeks of transplantation was increased by about 1.6 times or more in the group treated with CPNE4 protein (30%) compared to the control (Control, 18.1%).

Figure 4:
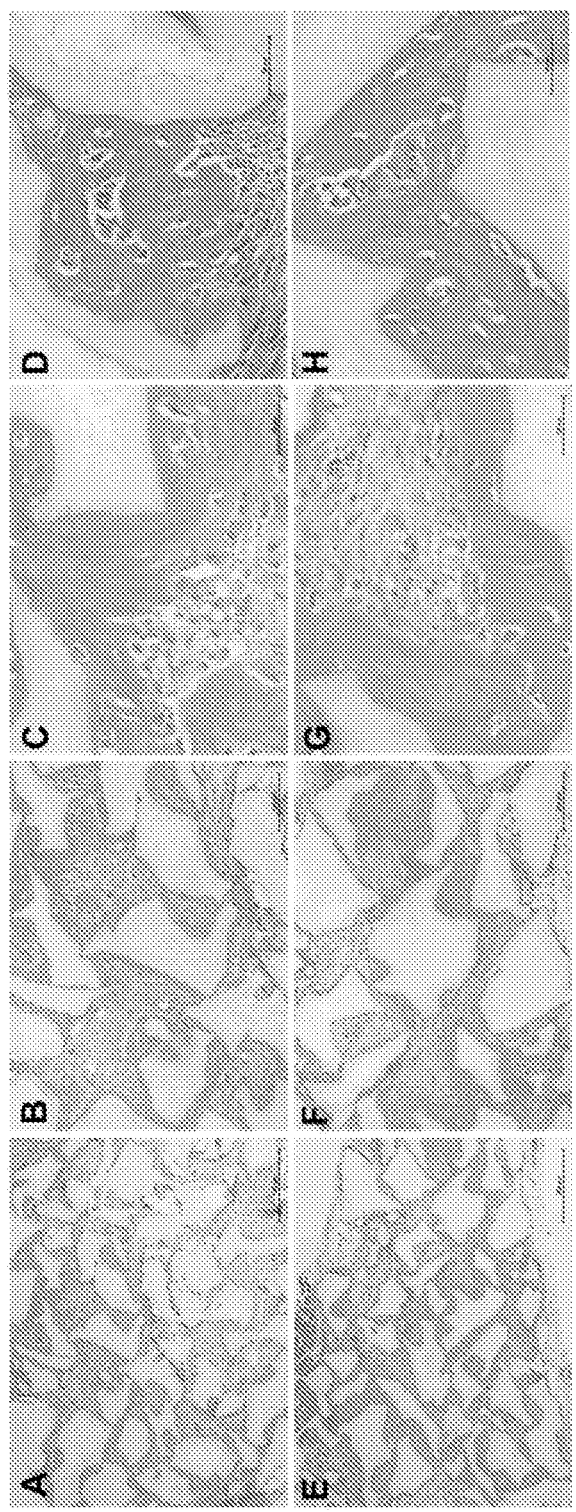
FIG. 4 shows microscopic images showing the histomorphological analysis of the hard tissue newly formed using human dental pulp cells (hDPCs) for 6 weeks in vivo, in which A to D show the results of transplantation of a control implant prepared by mixing hDPCs and 100 mg HA/TCP in a 0.5% fibrin gel for 6 weeks in a mouse with a compromised immune system, and in which E to H show the results of transplantation of implant prepared by mixing hDPCs and 100 mg HA/TCP, 5 μg CPNE4 protein in a 0.5% fibrin gel for 6 weeks in a mouse with a compromised immune system, respectively (scale bar: A, E 500 μm, B, F 200 μm, C, G 100 μm, D, H 50 μm).

FIG. 4 is a microscopic image showing the histomorphological analysis of new hard tissue formed using human dental pulp cells (hDPCs) for 6 weeks in vivo, A to D show the results of transplantation of a control implant prepared by mixing hDPCs and 100 mg HA/TCP in a 0.5% fibrin gel for 6 weeks in a mouse with compromised immune systems and E to H show the results of transplantation of hDPCs and 100 mg HA/TCP with 0.5% fibrin gel, respectively, together with 5 µg of CPNE4 protein, in a mouse with compromised immune systems for 6 weeks (scale bar: A, E 500 µm; B, F 200 µm; C, G 100 µm; D, H 50 µm).

As shown in FIG. 4, as a result of histomorphological analysis through hematoxylin-eosin staining, in the control group (FIG. 4A to FIG. 4D) not containing CPNE4 protein of the present invention and a group containing CPNE4 protein of the present invention were observed that bone-like tissue (FIG. 4E to FIG. 4H) and dentin-pulp-like tissue (FIG. 4C and FIG. 4G) were formed in the substrate of the calcified tissue around the HA/TCP particles.

(2) Collagen Staining Analysis

Collagen is the most abundant organic matrix in dentin, bone and cementum, and serves to accommodate deposited minerals. Accordingly, collagen staining was performed to confirm the accumulation of collagen protein in the calcified tissue formed in each control and experimental group.

Figure 5:
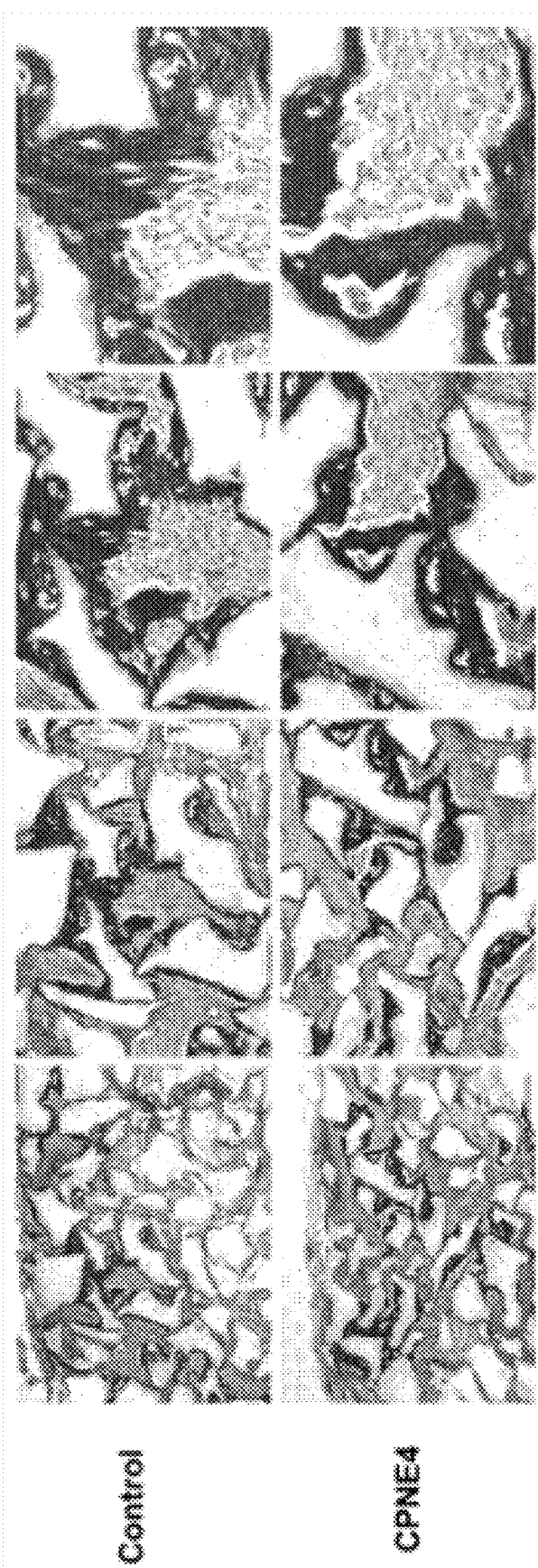
FIG. 5 shows microscopic images showing the level of collagen formation in hard tissue newly formed using human dental pulp cells (hDPCs) for 6 weeks in vivo, in which A to D show the results of transplantation of a control implant prepared by mixing hDPCs and 100 mg HA/TCP in a 0.5% fibrin gel for 6 weeks in a mouse with a compromised immune system, and in which E to H show the results of transplantation of implant prepared by mixing hDPCs, 100 mg HA/TCP, and 5 μg CPNE4 protein in a 0.5% fibrin gel for 6 weeks in a mouse with a compromised immune system, respectively (scale bar: A, E 500 μm, B, F 200 μm, C, G 100 μm, D, H 50 μm).

FIG. 5 shows microscopic images showing the level of collagen formation in newly formed hard tissue using human dental pulp cells (hDPCs) for 6 weeks in vivo, A to D show the results of transplantation of a control implant prepared by mixing hDPCs and 100 mg HA/TCP in a 0.5% fibrin gel for 6 weeks in a mouse with compromised immune systems and E to H show the results of transplantation of hDPCs and 100 mg HA/TCP with 0.5% fibrin gel, respectively, together with 5 µg of CPNE4 protein, in a mouse with compromised immune systems for 6 weeks (scale bar: A, E 500 µm; B, F 200 µm; C, G 100 µm; D, H 50 µm). The formed hard tissue was stained by the method of collagen stain (Masson's trichrome stain).

As shown in FIG. 5, compared to the control group (FIG. 5A to 5D), in the group containing CPNE4 protein of the present invention (FIG. 5E to 5H), it was confirmed that the formation level of collagen was increased (i.e., increasing accumulation of collagen protein).

On the other hand, human dental pulp stem cells (hDPSCs) are known to be capable of differentiating odontoblast and generating dentin, and differentiating osteoblast and generating bone, and recently human dental pulp cells are confirmed that it can differentiate into cementoblast-like cells, adipocytes and collagen-forming cells capable of regenerating periodontal tissues containing cementum in compromised mouse or rat (Stem Cells Int. 2016; 2016: 4709572. doi: 10.1155/2016/4709572, J Oral Implantol. 2013; 39(4):433-43). The collagen fiber bundle is inserted into the calcified cementum by horizontal or inclined direction. Therefore, in the present invention, after 6 weeks of transplantation, a portion of human dental pulp cells differentiated into cementum-like tissue was confirmed through collagen staining.

Figure 6:
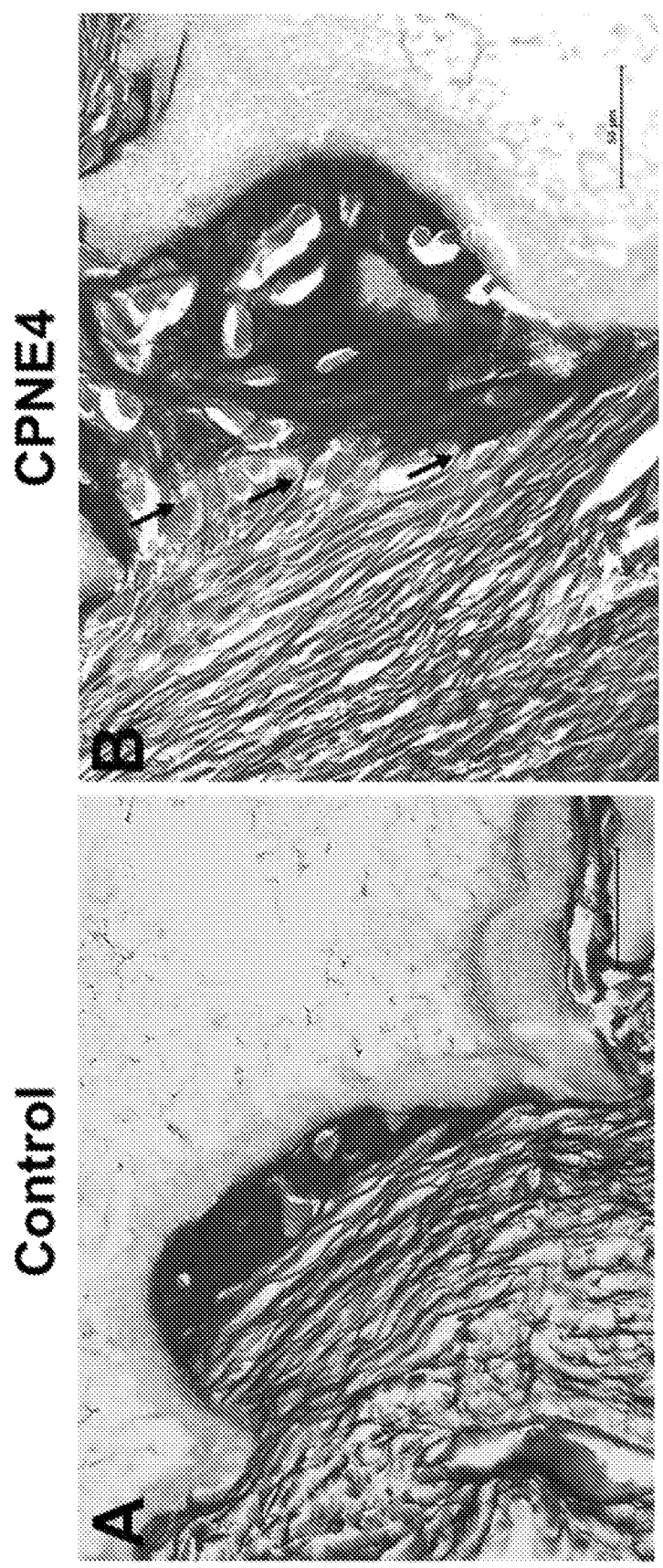
FIG. 6 shows microscopic images showing cementum-like tissue and periodontal tissue-like collagen fiber bundles attached to cementum-like tissue by collagen staining method in hard tissue newly formed using human dental pulp cells (hDPCs) for 6 weeks in vivo, in which A shows the results of transplantation of a control implant prepared by mixing hDPCs and 100 mg HA/TCP in a 0.5% fibrin gel for 6 weeks in a mouse with a compromised immune system, and in which B shows the results of transplantation of implant prepared by mixing hDPCs, 100 mg HA/TCP, and 5 μg CPNE4 protein in a 0.5% fibrin gel for 6 weeks in a mouse with a compromised immune system, respectively. The scale bar is 50 μm.

FIG. 6 shows that a bundle of cementum-like tissue and periodontal tissue-like collagen fiber bundles were attached to cementum-like tissue by collagen staining method in newly formed hard tissue using human dental pulp cells (hDPCs) for 6 weeks in vivo, in which A shows the results of transplantation of a control implant prepared by mixing hDPCs and 100 mg HA/TCP in a 0.5% fibrin gel for 6 weeks in a mouse with a compromised immune system, and in which B shows the results of transplantation of implant prepared by mixing hDPCs, 100 mg HA/TCP, and 5 µg CPNE4 protein in a 0.5% fibrin gel for 6 weeks in a mouse with a compromised immune system, respectively. The scale bar is 50 µm. The formed hard tissue was stained by the method of collagen stain (Masson's trichrome stain).

As shown in FIG. 6, in the control group (A of FIG. 6), the form in which the collagen fiber bundle was horizontally inserted into the newly formed calcified tissue was not observed, however in the CPNE4 protein treated group (FIG. 6B), the form in which the collagen fiber bundle was inserted in horizontal or inclined direction into the newly formed calcified tissue was observed in hard tissue.

(3) Immunohistochemical Analysis

The expression of DSP, odontoblast specific differentiation marker gene, was confirmed by immunohistochemical analysis.

Figure 7:
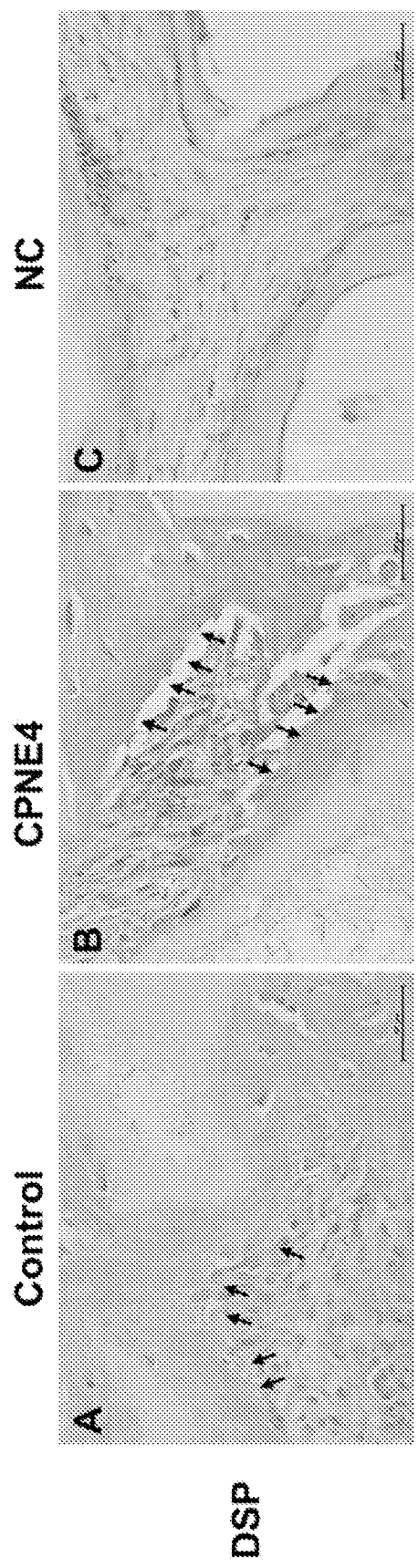
FIG. 7 shows immunostaining images showing the immunohistochemical analysis of the expression level of DSP, odontoblast differentiation marker gene, using immunostaining method, in hard tissue newly formed using human dental pulp cells (hDPCs) for 6 weeks in vivo, in which A shows the results of transplanting the implant prepared by mixing hDPCs and 100 mg HA/TCP in a 0.5% fibrin gel in a mouse with a compromised immune system for 6 weeks, in which B shows the results of transplanting the implant prepared by mixing hDPCs 100 mg HA/TCP, and 5 µg CPNE4 protein in a 0.5% fibrin gel in a mouse with a compromised immune system for 6 weeks. A and B are immunostained of the formed hard tissue using an anti-DSP antibody. C is a negative control of immunohistochemical analysis treated only with secondary antibodies. Arrows in A and B indicate the expression of DSP in newly formed calcified tissue. The scale bar is 50 µm.

FIG. 7 is an immunostaining picture of immunohistochemical analysis. Newly formed hard tissue by human dental pulp cells (hDPCs) for 6 weeks in vivo was used for the analysis of the expression level of DSP, a marker for differentiation of odontoblast using immunostaining method, A to D show the results of transplantation of a control implant prepared by mixing hDPCs and 100 mg HA/TCP in a 0.5% fibrin gel for 6 weeks in a mouse with compromised immune systems and E to H show the results of transplantation of hDPCs and 100 mg HA/TCP with 0.5% fibrin gel, respectively, together with 5 µg of CPNE4 protein, in a mouse with compromised immune systems for 6 weeks. A and B were immunostained using the anti-DSP antibody. C is a negative control of immunohistochemical analysis treated with only secondary antibodies. Arrows marked A and B indicate the expression of DSP in newly formed calcified tissue.

As shown in FIG. 7, the control group (FIG. 6A) was weakly expressed in DSP in newly formed dentin-pulp-like tissue, but the calcified tissue in which DSP was newly formed in the group containing CPNE4 protein of the present invention (FIG. 6B) was strongly expressed. FIG. 7C shows that in the immunohistochemical analysis, the secondary antibody-treated negative control group was not stained with DSP.

Example 2-5. Cell Analysis Using Scanning Electron Microscope of Transplanted Tissue Scanning electron microscope analysis of the method of Example 1-5 was performed to confirm the differentiation of human dental pulp cells (hDPCs) into odontoblast, osteoblast and/or cementoblast in the control group and the experimental group treated with the CPNE4 protein for 6 weeks after transplantation.

FIG. 8 shows an SEM image showing the analysis of newly formed hard tissue using human dental pulp cells (hDPCs) for 6 weeks in vivo by a scanning electron microscope (SEM), in which A and B show the results of transplantation of a control implant prepared by mixing hDPCs and 100 mg HA/TCP in a 0.5% fibrin gel for 6 weeks in a mouse with a compromised immune system, and in which C and D show the results of transplantation of implant prepared by mixing hDPCs, 100 mg HA/TCP, and 5 μg CPNE4 protein in a 0.5% fibrin gel for 6 weeks in a mouse with a compromised immune system, respectively. The scale bar is 10 μm. The formed hard tissue was observed with a scanning electron microscope.

As shown in FIG. 8, in the control group treated with hDPCs-only, some of the osteoblast-like cells (A in FIG. 8) or the odontoblast-like cells (in FIG. 8B) with incomplete odontoblastic processes cells were formed around the formed hard tissue. In the CPNE4 protein-treated group, odontoblast-like cells were observed along the formed hard tissue, and the odontoblastic processes were also extended toward the formed hard tissue (FIGS. 8C and D).

Example 2-6. Hard Tissue Formation of Human Dental Pulp Cells (hDPCs) by CPNE4 Protein In Vivo for 12 Weeks (1) Histomorphological Analysis Except for raising the implanted mouse for 12 weeks, the method of Example 2-4 was performed to analyze hard tissue formation in human dental pulp cells.

Figure 9:
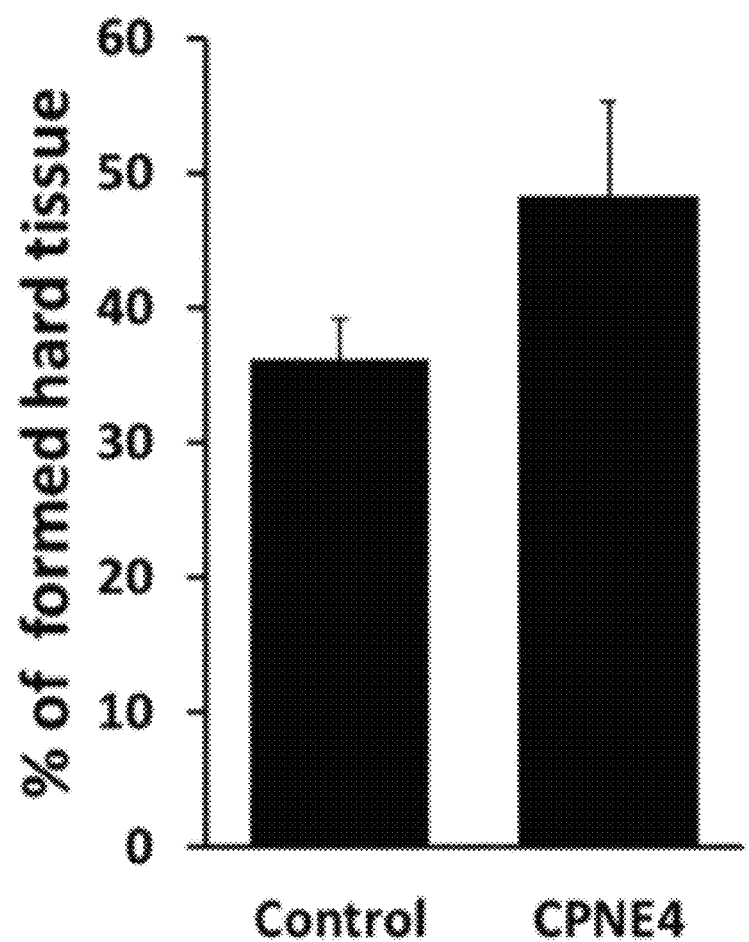
FIG. 9 shows the result of measuring the amount of newly formed hard tissue using human dental pulp cells (hDPCs) for 12 weeks in vivo.

FIG. 9 shows the results of measuring the amount of newly formed hard tissue using human dental pulp cells (hDPCs) for 12 weeks in vivo. As shown in FIG. 9, the ratio of hard tissue formation after 12 weeks of transplantation was increased by about 1.3 times or more in the group treated with CPNE4 protein (48.2%) compared to the control (Control, 36.1%).

Figure 10:
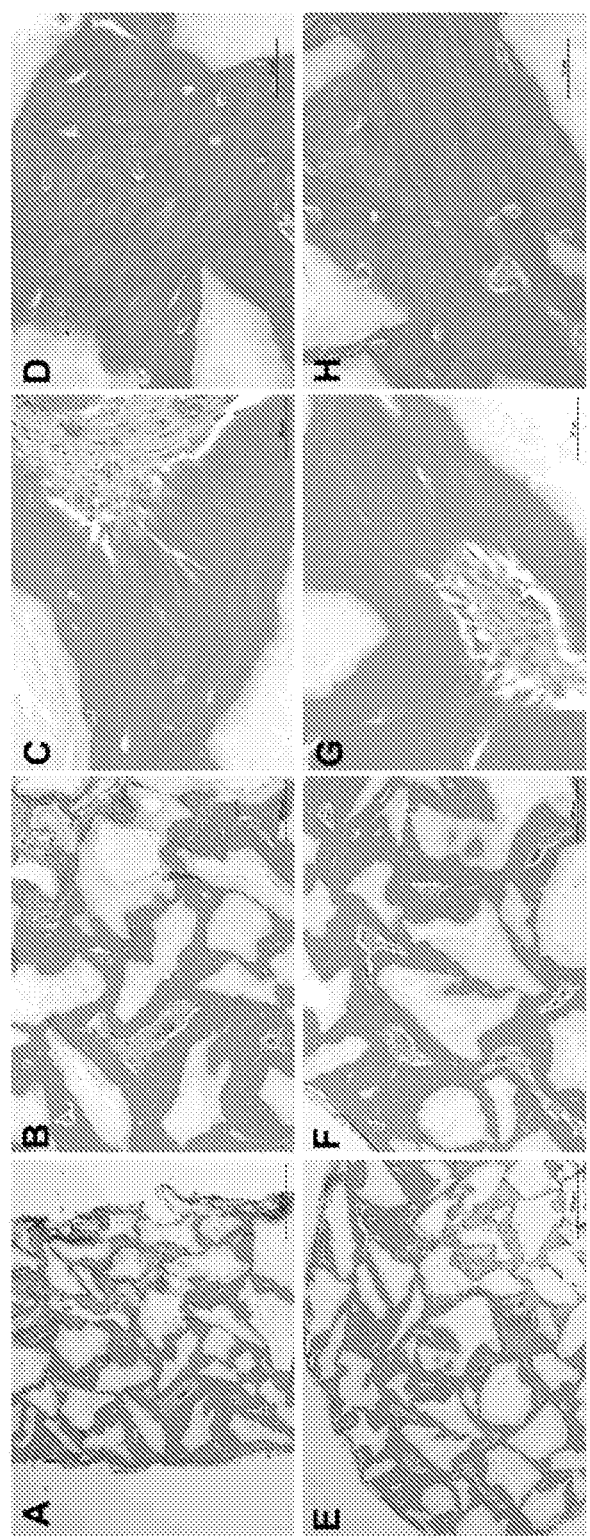
FIG. 10 shows microscopic images showing the histo-morphological analysis of the hard tissue formed using human dental pulp cells (hDPCs) for 12 weeks in vivo, in which A to D show the results of transplantation of a control implant prepared by mixing hDPCs and 100 mg HA/TCP in a 0.5% fibrin gel for 12 weeks in a mouse with a compromised immune system, and in which E to H show the results of transplantation of implant prepared by mixing hDPCs and 100 mg HA/TCP, 5 µg CPNE4 protein in a 0.5% fibrin gel for 12 weeks in a mouse with a compromised immune system, respectively (scale bar: A, E 500 µm, B, F 200 µm, C, G 100 µm, D, H 50 µm).

FIG. 10 is a microscopic image showing the histomorphological analysis of the hard tissue formed using human dental pulp cells (hDPCs) for 12 weeks in vivo, A to D show the results of transplantation of a control implant prepared by mixing hDPCs and 100 mg HA/TCP in a 0.5% fibrin gel for 12 weeks in a mouse with compromised immune systems and E to H show the results of transplantation of hDPCs and 100 mg HA/TCP with 0.5% fibrin gel, respectively, together with 5 μg of CPNE4 protein, in a mouse with compromised immune systems for 12 weeks (scale bar: A, E 500 μm; B, F 200 μm; C, G 100 μm; D, H 50 μm).

As shown in FIG. 10, as a result of histomorphological analysis through hematoxylin-eosin staining, similar to the case of FIG. 4 (6 weeks transplant) in the control group (FIG. 8A to FIG. 8D) not containing CPNE4 protein of the present invention and a group containing CPNE4 protein of the present invention (FIG. 8E to FIG. 8H) were observed that bone-like tissue (FIG. 10C and FIG. 10G) and dentin-pulp-like tissue were newly formed in the substrate of the calcified tissue around the HA/TCP particles (FIG. 10D and FIG. 10H).

Collagen staining was performed to confirm the accumulation of collagen protein in the calcified tissue formed in each control group and experimental group.

Figure 11:
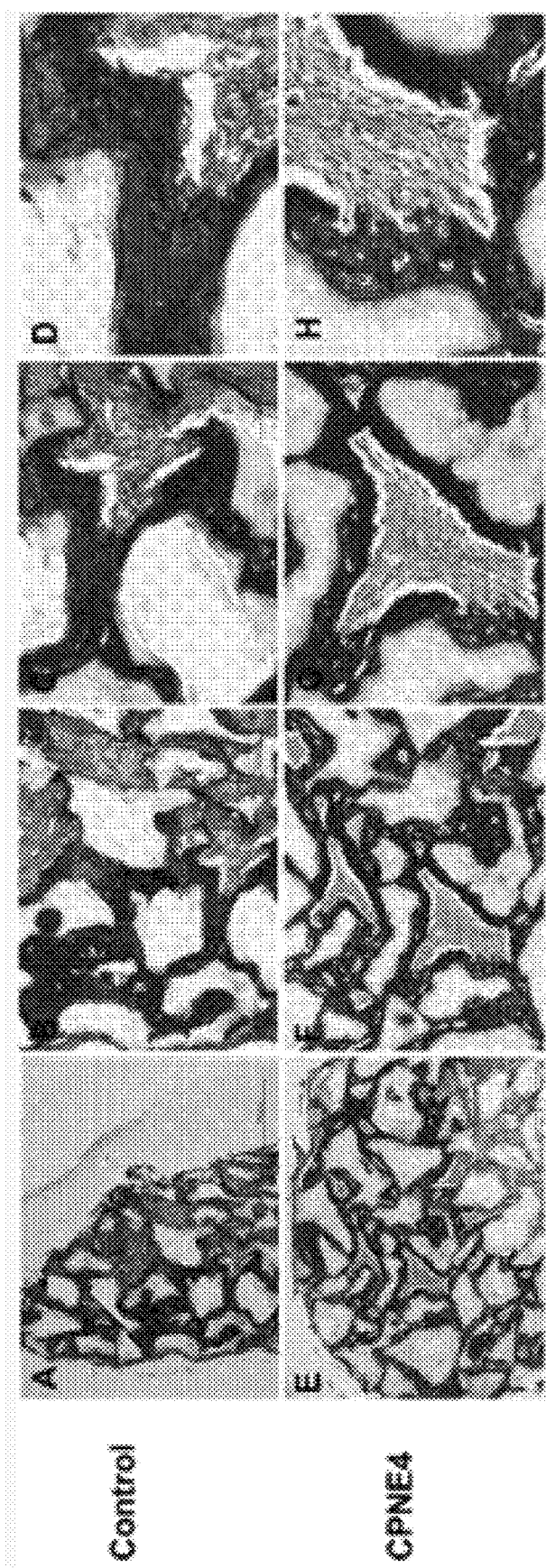
FIG. 11 shows microscopic images showing the level of collagen formation in hard tissue formed using human dental pulp cells (hDPCs) for 12 weeks in vivo, in which A to D show the results of transplantation of a control implant prepared by mixing hDPCs and 100 mg HA/TCP in a 0.5% fibrin gel for 12 weeks in a mouse with a compromised immune system, and in which E to H show the results of transplantation of implant prepared by mixing hDPCs, 100 mg HA/TCP, and 5 µg CPNE4 protein in a 0.5% fibrin gel for 12 weeks in a mouse with a compromised immune system, respectively (scale bar: A, E 500 µm, B, F 200 µm, C, G 100 µm, D, H 50 µm).

FIG. 11 shows microscopic images showing the level of collagen formation in hard tissue formed using human dental pulp cells (hDPCs) for 12 weeks in vivo, A to D show the results of transplantation of a control implant prepared by mixing hDPCs and 100 mg HA/TCP in a 0.5% fibrin gel for 12 weeks in a mouse with compromised immune systems and E to H show the results of transplantation of hDPCs and 100 mg HA/TCP with 0.5% fibrin gel, respectively, together with 5 μg of CPNE4 protein, in a mouse with compromised immune systems for 12 weeks (scale bar: A, E 500 μm; B, F 200 μm; C, G 100 μm; D, H 50 μm). The formed hard tissue was stained by the method of collagen stain (Masson's trichrome stain).

As shown in FIG. 11, compared to the control group (FIGS. 11A to 11D), in the group containing CPNE4 protein of the present invention (FIGS. 11E to 11H), it was confirmed that the formation level of collagen was increased (i.e., increasing accumulation of collagen protein).

After that, newly formed calcified cementum-like tissue differentiated from human dental pulp cell was confirmed through collagen staining for 12 weeks in vivo.

Figure 12:
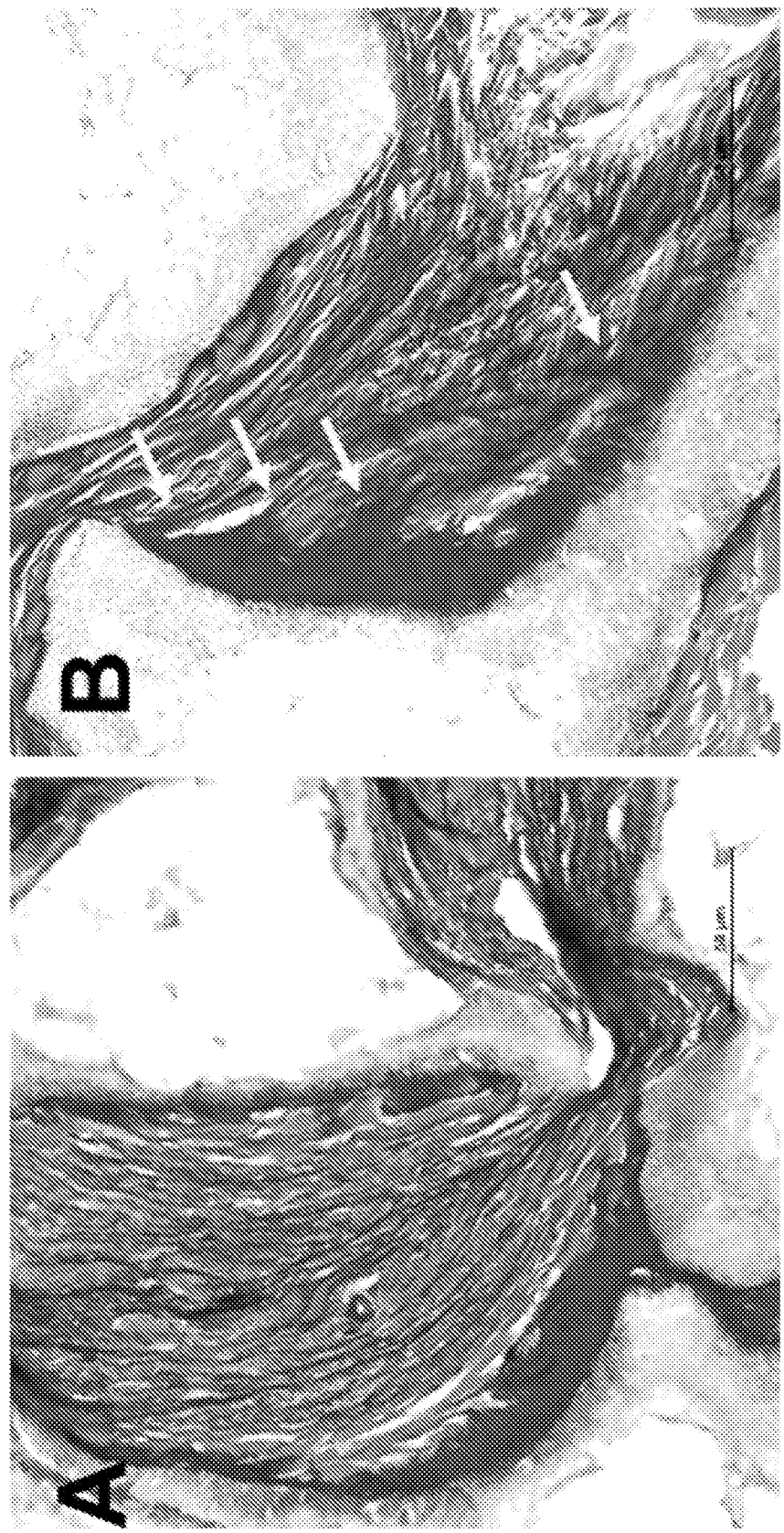
FIG. 12 Shows microscopic images showing cementum-like tissue and periodontal tissue-like collagen fiber bundles attached to cementum-like tissue by collagen staining method in hard tissue newly formed using human dental pulp cells (hDPCs) for 12 weeks in vivo, in which A shows the results of transplantation of a control implant prepared by mixing hDPCs and 100 mg HA/TCP in a 0.5% fibrin gel for 6 weeks in a mouse with a compromised immune system, and in which B shows the results of transplantation of implant prepared by mixing hDPCs, 100 mg HA/TCP, and 5 µg CPNE4 protein in a 0.5% fibrin gel for 12 weeks in a mouse with a compromised immune system, respectively. The scale bar is 50 µm.

FIG. 12 Shows microscopic images showing cementum-like tissue and periodontal tissue-like collagen fiber bundles attached to cementum-like tissue by collagen staining method in hard tissue newly formed using human dental pulp cells (hDPCs) for 12 weeks in vivo, in which A shows the results of transplantation of a control implant prepared by mixing hDPCs and 100 mg HA/TCP in a 0.5% fibrin gel for 6 weeks in a mouse with a compromised immune system, and in which B shows the results of transplantation of implant prepared by mixing hDPCs, 100 mg HA/TCP, and 5 μg CPNE4 protein in a 0.5% fibrin gel for 12 weeks in a mouse with a compromised immune system, respectively. The scale bar is 50 μm. The formed hard tissue was stained by the method of collagen stain (Masson's trichrome stain).

As shown in FIG. 12, in the control group (A of FIG. 12), the form in which the collagen fiber bundle was horizontally inserted into the newly formed calcified tissue was not observed, however in the CPNE4 protein treated group (FIG. 12B), the form in which the collagen fiber bundle was inserted in the horizontal or inclined direction into the newly formed calcified tissue was observed in hard tissue.

(3) Immunohistochemical Analysis

The expression of DSP, odontoblast specific differentiation marker gene, was confirmed by immunohistochemical analysis.

FIG. 13 is an immunostaining picture of immunohistochemical analysis. Newly formed hard tissue by human pulp cells (hDPCs) for 12 weeks in vivo was used for the analysis of the expression level of DSP, a marker for differentiation of odontoblast using immunostaining method, A to D show the results of transplantation of a control implant prepared by mixing hDPCs and 100 mg HA/TCP in a 0.5% fibrin gel for 12 weeks in a mouse with compromised immune systems and E to H show the results of transplantation of hDPCs and 100 mg HA/TCP with 0.5% fibrin gel, respectively, together with 5 μg of CPNE4 protein, in a mouse with compromised immune systems for 12 weeks. A and B were immunostained using the anti-DSP antibody. C is a negative control of immunohistochemical analysis treated with only secondary antibodies. Arrows marked A and B indicate the expression of DSP in newly formed calcified tissue.

As shown in FIG. 13, the control group (FIG. 13A) was weakly expressed in DSP in newly formed dentin-pulp-like tissue, but the calcified tissue in which DSP was newly formed in the group containing CPNE4 protein of the present invention (FIG. 13B) was strongly expressed. FIG. 7C shows that in the immunohistochemical analysis, the secondary antibody-treated negative control group was not stained with DSP.

Summarizing the results of Examples 2-4 and 2-6, it was found that CPNE4 protein of the present invention exhibits an effect capable of promoting regeneration of dentin/pulp tissue complexes and bone/cementum-like tissues.

This study was supported by the Korea Evaluation Institute of Industrial Technology (KEIT) and funded by the Ministry of Trade, Industry & Energy in 2017 (10078369).

While one or more embodiments of the present invention have been described with reference to the figures, it will be understood by those of ordinary skill in the art that various changes in form and details may be made therein without departing from the spirit and scope of the present invention.

The invention claimed is:

1. A method for preventing and/or treating dentin-dental pulp disease or periodontal diseases in a subject in need thereof, comprising administering an effective amount of a composition comprising a copine-4 (CPNE4) protein to the subject.

2. The method of claim 1, wherein the administering of the composition promotes regenerating a hard tissue selected from dentin, bone and cementum, or dental pulp tissue.

3. The method of claim 1, wherein the administering of the composition promotes a differentiation of odontoblast, osteoblast, or cementoblast in a dental pulp cell.

4. The method of claim 1, wherein the administering of the composition promotes differentiation of non-dental mesenchymal stem cells into odontoblast, osteoblast, or cementoblast.

5. The method of claim 1, wherein the composition is a pharmaceutical composition and further comprises a pharmaceutically acceptable carrier, excipient, or diluent.

6. The method of claim 1, wherein the dentin-dental pulp disease is one or more selected from the group consisting of dentin hypersensitivity, pulp hyperemia, pulpitis, pulp degeneration, pulp necrosis, and gangrenous pulp.

7. The method of claim 1, wherein the periodontal disease is one or more selected from the group consisting of gingivitis, periodontitis, periodontal pocket, and periodontal abscess.

8. The method of claim 1, wherein the composition is a dietary supplement.

9. The method of claim 1, wherein the composition is a foodstuff.

10. A method for regenerating a hard tissue in vitro comprising contacting the hard tissue with a copine-4 (CPNE4) protein,
wherein the hard tissue is one or more selected from the group consisting of dentin, bone and cementum, and dental pulp tissue.

11. The method of claim 10, wherein the contacting is carried out by transplanting the copine-4 (CPNE4) protein to the hard tissue.

12. A method for promoting differentiation of non-dental mesenchymal stem cells into odontoblast, osteoblast, or cementoblast in vitro, comprising transplanting the non-dental mesenchymal stem cells with copine-4 (CPNE4) protein to the non-dental mesenchymal stem cell.

13. A method for preventing and/or treating dentin-dental pulp disease or periodontal diseases in a subject in need thereof, comprising administering an effective amount of a composition comprising a polynucleotide encoding copine-4 (CPNE4) protein to the subject.

14. The method of claim 13, wherein the administering of the composition promotes regenerating a hard tissue selected from dentin, bone and cementum, or dental pulp tissue.

15. The method of claim 13, wherein the administering of the composition promotes a differentiation of odontoblast, osteoblast, or cementoblast in a dental pulp cell.

16. The method of claim 13, wherein the administering of the composition promotes differentiation of non-dental mesenchymal stem cells into odontoblast, osteoblast, or cementoblast.

17. The method of claim 13, wherein the composition is a pharmaceutical composition and further comprises a pharmaceutically acceptable carrier, excipient, or diluent.

18. The method of claim 13, wherein the dentin-dental pulp disease is one or more selected from the group consisting of dentin hypersensitivity, pulp hyperemia, pulpitis, pulp degeneration, pulp necrosis, and gangrenous pulp.

19. The method of claim 13, wherein the periodontal disease is one or more selected from the group consisting of gingivitis, periodontitis, periodontal pocket, and periodontal abscess.

20. The method of claim 13, wherein the composition is a dietary supplement or foodstuff.

21. A method for preventing and/or treating dentin-dental pulp disease or periodontal diseases in a subject in need thereof, comprising administering an effective amount of a composition comprising a vector comprising a polynucleotide encoding copine-4 (CPNE4) protein to the subject.

22. The method of claim 21, wherein the administering of the composition promotes regenerating a hard tissue selected from dentin, bone and cementum, or dental pulp tissue.

23. The method of claim 21, wherein the administering of the composition promotes a differentiation of odontoblast, osteoblast, or cementoblast in a dental pulp cell.

24. The method of claim 21, wherein the administering of the composition promotes differentiation of non-dental mesenchymal stem cells into odontoblast, osteoblast, or cementoblast.

25. The method of claim 21, wherein the composition is a pharmaceutical composition and further comprises a pharmaceutically acceptable carrier, excipient, or diluent.

26. The method of claim 21, wherein the dentin-dental pulp disease is one or more selected from the group consisting of dentin hypersensitivity, pulp hyperemia, pulpitis, pulp degeneration, pulp necrosis, and gangrenous pulp.

27. The method of claim 21, wherein the periodontal disease is one or more selected from the group consisting of gingivitis, periodontitis, periodontal pocket, and periodontal abscess.

28. The method of claim 21, wherein the composition is a dietary supplement or foodstuff.

29. A method selected from the group consisting of:
(a) method for regenerating a hard tissue in vitro comprising contacting the hard tissue with a polynucleotide encoding copine-4 (CPNE4) protein, wherein the hard tissue is one or more selected from the group consisting of dentin, bone and cementum, and dental pulp tissue; and
(b) method for promoting differentiation of non-dental mesenchymal stem cells into odontoblast, osteoblast, or cementoblast in vitro comprising transplanting the non-dental mesenchymal stem cells with a polynucleotide encoding copine-4 (CPNE4) protein to the non-dental mesenchymal stem cell.

30. A method selected from the group consisting of:
(a) method for regenerating a hard tissue in vitro comprising contacting the hard tissue with a vector comprising a polynucleotide encoding copine-4 (CPNE4) protein, wherein the hard tissue is one or more selected from the group consisting of dentin, bone and cementum, and dental pulp tissue; and
(b) method for promoting differentiation of non-dental mesenchymal stem cells into odontoblast, osteoblast, or cementoblast in vitro comprising transplanting the non-dental mesenchymal stem cells with a vector comprising a polynucleotide encoding copine-4 (CPNE4) protein to the non-dental mesenchymal stem cell.

* * * * *